United States Patent [19]
Balkwill et al.

[11] Patent Number: 4,695,131
[45] Date of Patent: Sep. 22, 1987

[54] DISUBSTITUTED ETHANES AND THEIR USE IN LIQUID CRYSTAL MATERIALS AND DEVICES

[76] Inventors: Peter H. Balkwill, 45 Cressingham Road, Reading, Berkshire; David I. Bishop, 19 Freshwater Drive,, Hamworthy, Poole, Dorset; Andrew D. Pearson, Flat 5, Ettrick House, Ettrick Road, Branksome Park, Poole, Dorset; Ian C. Sage, 238 Freshwater Drive, Hamworthy, Poole, Dorset; George W. Gray, 33 Newgate Street, Cottingham, Humberside; David Lacey, 19 Killdale Close, Hull, Humberside; Kenneth J. Toyne, 25 Hall Road, Hull, Humberside; Damien G. McDonnell, Flat 10, Eton Hurst, Upper Chase Road, Malvern, Worcester all of England

[21] Appl. No.: 573,819

[22] Filed: Jan. 25, 1984

[30] Foreign Application Priority Data

Jan. 26, 1983 [GB] United Kingdom ................. 8302119
Oct. 24, 1983 [GB] United Kingdom ................. 8328370

[51] Int. Cl.$^4$ ....................... G02F 1/13; C09K 19/30; C07C 25/18; C07C 43/19
[52] U.S. Cl. ........................... 350/350 R; 252/299.63; 252/299.5; 350/350 S; 568/659; 568/661; 570/129
[58] Field of Search ....................... 252/299.63, 299.5; 350/350 R, 350 S; 570/129; 568/642, 661, 659

[56] References Cited

U.S. PATENT DOCUMENTS

| | | | |
|---|---|---|---|
| 4,330,426 | 5/1982 | Eidenschink et al. | 252/299.63 |
| 4,331,552 | 5/1982 | Eidenschink et al. | 252/299.63 |
| 4,368,135 | 1/1983 | Osman | 252/299.63 |
| 4,393,258 | 7/1983 | Sato et al. | 252/299.63 |
| 4,400,293 | 8/1983 | Romer et al. | 252/299.63 |
| 4,405,488 | 9/1983 | Sugimori et al. | 252/299.63 |
| 4,415,470 | 11/1983 | Eidenschink et al. | 252/299.63 |
| 4,419,264 | 12/1983 | Eidenschink et al. | 252/299.63 |
| 4,439,015 | 3/1984 | Rich et al. | 252/299.63 |
| 4,479,885 | 10/1984 | Mukoh et al. | 252/299.63 |
| 4,482,472 | 11/1984 | Carr et al. | 252/299.62 |
| 4,490,305 | 12/1984 | Eidenschink et al. | 252/299.63 |
| 4,505,838 | 3/1985 | Romer et al. | 252/299.63 |
| 4,512,636 | 4/1985 | Andrews et al. | 252/299.61 |
| 4,551,264 | 11/1985 | Eidenschink et al. | 252/299.63 |
| 4,551,280 | 11/1985 | Sasaki et al. | 252/299.63 |
| 4,556,745 | 12/1985 | Carr et al. | 252/299.63 |
| 4,583,826 | 4/1986 | Petrzilka et al. | 252/299.63 |
| 4,594,465 | 6/1986 | Kam Minh Chan et al. | 252/299.66 |
| 4,602,851 | 7/1986 | Jenner et al. | 252/299.63 |
| 4,606,845 | 8/1986 | Romer et al. | 252/299.63 |
| 4,621,901 | 11/1986 | Petrzilka et al. | 252/299.63 |
| 4,637,897 | 1/1987 | Kelly | 252/299.63 |

FOREIGN PATENT DOCUMENTS

| | | | |
|---|---|---|---|
| 19665 | 12/1980 | European Pat. Off. | 252/299.63 |
| 58512 | 8/1982 | European Pat. Off. | 252/299.62 |
| 72204 | 2/1983 | European Pat. Off. | 252/299.62 |
| 74608 | 3/1983 | European Pat. Off. | 252/299.63 |
| 84194 | 7/1983 | European Pat. Off. | 252/299.63 |
| 2933563 | 2/1981 | Fed. Rep. of Germany | 252/299.63 |
| 2939782 | 4/1981 | Fed. Rep. of Germany | 252/299.64 |
| 3209178 | 9/1983 | Fed. Rep. of Germany | 252/299.61 |
| 3208089 | 9/1983 | Fed. Rep. of Germany | 252/299.63 |
| 3335550 | 4/1984 | Fed. Rep. of Germany | 252/299.63 |
| 58-8022 | 1/1983 | Japan | 252/299.63 |
| 59-16840 | 1/1984 | Japan | 252/299.63 |
| 59-42329 | 3/1984 | Japan | 252/299.63 |
| 2041915 | 9/1980 | United Kingdom | 252/299.66 |
| 2107733 | 5/1983 | United Kingdom | 252/299.63 |
| 2134110 | 8/1984 | United Kingdom | 252/299.63 |

OTHER PUBLICATIONS

Gray, G. W., et al, Mol. Cryst. Liq. Cryst., vol. 67, No. 1-4, pp. 1-24 (1981).
Kelly, S. M., et al, Helvetica Chimica Acta, vol. 68, pp. 1444-1452 (1985).

*Primary Examiner*—Teddy S. Gron
*Attorney, Agent, or Firm*—Stevens, Davis, Miller & Mosher (Abstract continued on next page.)

[57] ABSTRACT

A fluorinated compound having a formula:

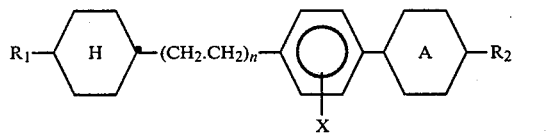   I wherein:

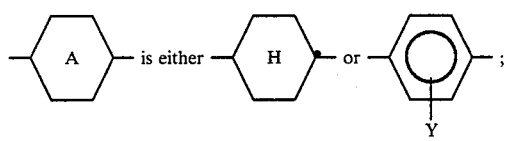

$R_1$ is hydrogen or alkyl having up to 12 carbon atoms;
$R_2$ is selected from hydrogen, alkyl having up to 12 carbon atoms, alkoxy having up to 12 carbon atoms,

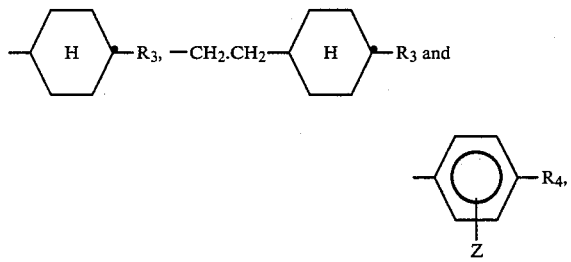

wherein $R_3$ is hydrogen or alkyl having up to 12 carbon atoms, and wherein $R_4$ is hydrogen, alkyl having up to 12 carbon atoms or alkoxy having up to 12 carbon atoms;

represents a cyclohexane ring which is in the trans configuration if 1, 4-disubstituted;

represents a benzene ring;
each of X, Y and Z independently represents hydrogen or fluorine in one or more of the lateral benzene ring positions, provided that at least one of X, Y and Z is present representing fluorine;
n=0 or 1 provided that when n=0

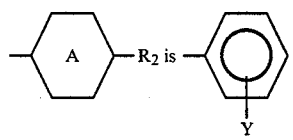

and $R_1$ is alkyl;
with the proviso that in Formula I when n is 1 and

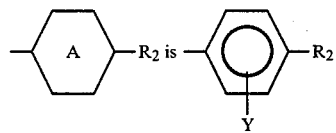

where $R_1$ is n-alkyl and $R_2$ is n-alkyl or n-alkoxy the total number of carbon plus oxygen atoms in the two groups $R_1$ and $R_2$ is less than 10.

13 Claims, 7 Drawing Figures

DISUBSTITUTED ETHANES AND THEIR USE IN LIQUID CRYSTAL MATERIALS AND DEVICES

The present invention relates to disubstituted ethanes and their use in liquid crystal materials and devices.

The use of liquid crystal materials to exhibit electro-optical effects in display devices such as digital calculators, watches, meters and simple word displays is now well known. However known liquid crystal materials are not ideal in all respects and a considerable amount of work is currently being carried out in the art to improve their properties.

Liquid crystal materials normally consist of generally selected mixture compositions and improved materials are obtained by forming new mixtures having an improved combination of properties.

The composition of a liquid crystal mixture for electro-optical applications depends on the kind of display effect to be utilised and the particular properties required for that effect. Examples of various display effects are given below. For all kinds however, it is desirable for the mixture to show the best possible combination of certain general properties, eg as follows:

(i) a liquid crystalline temperature range—including room temperature (20° C.)—which is as wide as possible;
(ii) a melting point (solid-to-liquid crystal transition temperature) which is as low as possible;
(iii) a clearing point (liquid crystalline to isotropic liquid transition temperature) which is as high as possible;
(iv) a positive or negative (as appropriate) dielectric anisotropy (permittivity measured parallel to the molecular axis less that measured perpendicular to the molecular axis) which is as great as possible in order to minimise the display voltage;
(v) a viscosity which is as low as possible in order to minimise the display switching speeds;
(vi) an electro-optical response which varies as little as possible with temperatures;
(vii) a good chemical and photochemical stability.

Examples of further particular properties useful in specific applications are as follows:

(viii) a good multiplexibility;
(ix) an ability to switch dielectric anisotropy with frequency; and
(x) a birefringence of selected magnitude.

The required combination of properties of a liquid crystal mixture composition is obtained by blending together components of different properties in the mixture.

One combination of properties which is particularly difficult to achieve is that required for displays to be used on dashboards in automobiles, where a low viscosity essential for fast switching at temperatures as low as −20° to −30° C. must be combined with a high clearing point (>90° C.) and a high birefringence to prevent "bleed through" of light from the rear illumination through parts of the display that are off.

In order to keep production costs to a minimum it is desirable to use the smallest number of components in the mixture consistent with the achievement of a satisfactory combination of the required properties. Therefore it is desirable that the individual components used show a number of the required properties. It is desirable that the mutual solubility of the individual component is good, also in order to minimise the number of components.

The purpose of the present invention is to provide a class of novel liquid crystal compounds which provide suitable components for liquid crystal mixture compositions for electro-optical displays, particularly displays to be used on dashboards in automobiles.

According to the present invention in a first aspect there is provided a fluorinated compound having a formula:

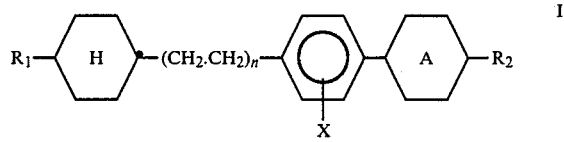

wherein:

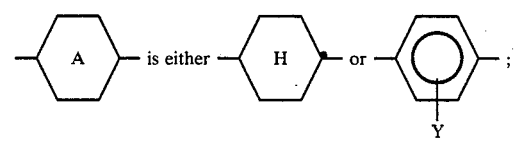

$R_1$ is hydrogen or alkyl having up to 12 carbon atoms;
$R_2$ is selected from hydrogen, alkyl having up to 12 carbon atoms, alkoxy having up to 12 carbon atoms,

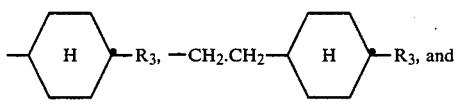

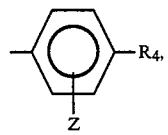

wherein $R_3$ is hydrogen or alkyl having up to 12 carbon atoms, and wherein $R_4$ is hydrogen, alkyl having up to 12 carbon atoms or alkoxy having up to 12 carbon atoms;

represents a cyclohexane ring which is in the trans configuration if 1,4-disubstituted;

represents a benzene ring;
each of X, Y, and Z independently represents hydrogen or fluorine in one or more of the lateral benzene ring positions, provided that at least one of X, Y and Z is present representing fluorine;
$n=0$ or 1 provided that when $n=0$

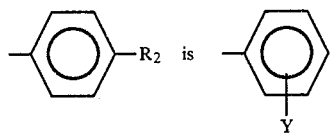

and $R_1$ is alkyl;
with the proviso that in Formula I when n is 1 and

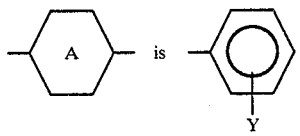

wherein $R_1$ is n-alkyl and $R_2$ is n-alkyl or n-alkoxy the total number of carbon atoms or carbon plus oxygen atoms in the two groups $R_1$ and $R_2$ is less than 10.

For use in nematic liquid crystal mixtures each alkyl or alkoxy group included in the compound of Formula I is preferably straight chained. However for use in chiral nematic (optically active) mixtures one or more alkyl or alkoxy groups contained in the molecule may be a chiral group, eg of the form $(+)-CH_3(CH_2)_nCH(CH_3)CH_2$, where n is from 1 to 8 and $(+)-$ represents a chiral group having a positive optical rotation angle, eg $(+)$-2-methylbutyl.

Examples of some sub-classes of compound embraced by Formula I, including preferred sub-classes, are as follows:

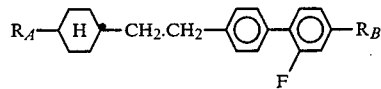

Formula Ia

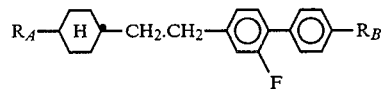

Formula Ib

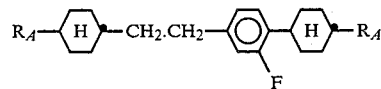

Formula Ic

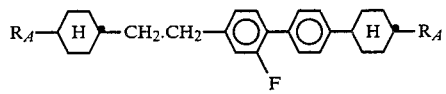

Formula Id

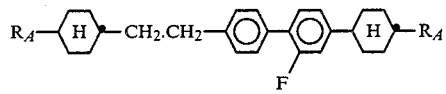

Formula Ie

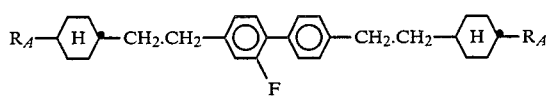

Formula If

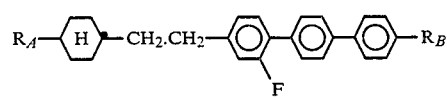

Formula Ig

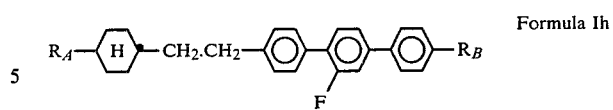

Formula Ih

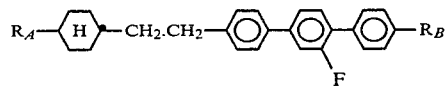

Formula Ii

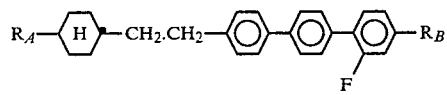

Formula Ij where each $R_A$ is independently alkyl, for instance n-alkyl having 1 to 12, eg 1 to 8 carbon atoms and each $R_B$ is independently hydrogen, alkyl or alkoxy, for instance n-alkyl or n-alkoxy having 1 to 12, eg 1 to 8 carbon atoms.

For compounds of Formula Ia and Ib above the proviso specified above applies, namely that if $R_A$ is n-alkyl and $R_B$ is n-alkyl or n-alkoxy the total number of carbon plus oxygen atoms (if any) in the two groups is less than 10. Preferably the total number of carbon plus oxygen atoms in the two groups $R_A$ and $R_B$ is between 4 and 8 inclusive.

Compounds having the same generalised formulae as Formulae Ia and Ib but wherein the terminal n-alkyl groups or n-alkyl and n-alkoxy groups have a total of ten carbon atoms and ten carbon plus oxygen atoms respectively are proposed in European Patent Application No. 84194 published after the filing of UK Patent Application No. 8302119 from which priority is claimed herein. However no properties are disclosed or suggested for these proposed compounds in the said European Application. However, it is shown below that these compounds are considerably inferior to the corresponding compounds of Formulae Ia and Ib (to which the above proviso applies and which are not proposed in the said European Application) in terms of their injected smectic behaviour in mixtures with positive nematic compounds as explained below. The compounds proposed in said European Application are therefore excluded from the scope of the present invention.

Compounds of Formulae Ia to Ij specified above in general are examples of compounds of Formula I which are useful as liquid crystal compounds whilst compounds of Formula Ik as follows:

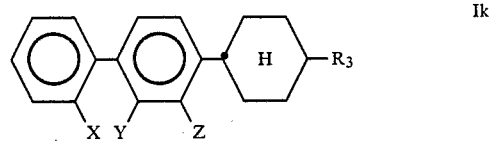

Ik are examples of compounds useful as intermediates in the synthesis of certain liquid crystal compounds of Formula I, particularly compounds of Formula Id and Ie, wherein X, Y and Z are H or F at least one being F.

Compounds of Formula I can provide very attractive components of liquid crystal materials for electro-optical display applications. For example, compounds of the sub-classes of Formulae Ia and Ib above, wherein $R_A$ and $R_B$ are n-alkyl groups, show the properties described in the Examples and Tables below, where in certain preferred examples the following highly advantageous points can be noticed:

(i) low melting points, generally less than 30° C., which are advantageous in the formulation of liquid crystalline mixtures with low melting point;
(ii) high clearing points in the vicinity of 100° C., and an extraordinarily wide nematic range often of about 70 Celsius degrees, which are advantageous in the formulation of liquid crystalline mixtures with wide nematic range;
(iii) the virtual absence of highly undesirable smectic phases;
(iv) little tendency to form smectic phases in combination with nematic materials of positive dielectric anisotropy;
(v) a high solubility in nematic materials of positive dielectric anisotropy;
(vi) the property of elevating the clearing point when added to mixtures with positive nematic materials already containing a high clearing point component;
(vii) a relatively low viscosity and the property of reducing the viscosity of known nematic mixtures;
(viii) the ability to form the basis of mixtures with fast switching times at low temperatutes;
(ix) a higher birefringence in comparison with other known materials with equivalent thermal and viscous properties:
(x) a very low temperature dependence of threshold voltage;
(xi) good chemical and photochemical stability.

Such an attractive combination of properties offers the possibility of forming liquid crystal mixtures having properties superior to any known mixtures.

Liquid crystal compounds containing the grouping

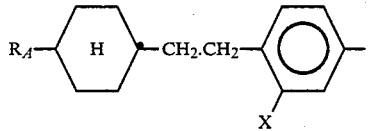

where $R_A$ and X are as defined above, are known, see for example, Published UK Patent Specification Nos 2023136A and 2093057A. However, in general, the novel compounds of Formula I, in particular those of Formula Ia and Ib unexpectedly show a better overall combination of desirable properties than such known compounds.

For example, the compounds of Formula I can have a higher clearing point, without a significant corresponding increase in melting point and viscosity, compared with the known compounds of Formula A as follows:

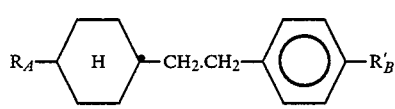

Formula A where $R'_B$ is alkyl, alkoxy or cyano.

Likewise, the compounds of Formula I have a lower melting point and viscosity and a better solubility in positive nematic materials than the known high clearing point additives of formula B and C as follows:

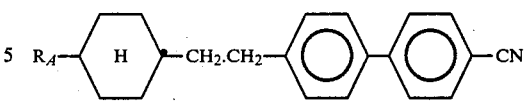

Formula B

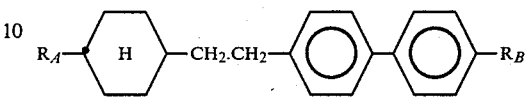

Formula C

Furthermore the compounds of Formula I are generally more versatile than the compounds of Formula B and may be added to or used as materials of negative dielectric anisotropy (as well as those of positive dielectric anisotropy) for use in certain specific applications described below. The compounds of Formula B are not generally suitable for this purpose because they have a high positive dielectric anisotropy.

By far the most remarkable property of the compounds of Formula I is the effect of the lateral fluorine atom in suppressing and eliminating undesirable smectic phases. This may be seen most readily by comparing the phase transitions of compounds without, and with the lateral fluorine atoms, in Tables 1 and 2 as follows:

TABLE 1

Comparative properties of compounds having the formula:

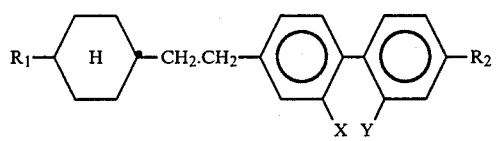

| $R_1$ | $R_2$ | X | Y | K—N | K—S | S—S | S—N | N—I |
|---|---|---|---|---|---|---|---|---|
| $C_2H_5$ | $C_3H_7$ | H | H | | 55 | | 98.5 | 121.5 |
| $C_2H_5$ | $C_3H_7$ | H | F | 21.3 | | | | 78.3–78.5 |
| $C_3H_7$ | $C_3H_7$ | H | H | | 67 | 118 | 119 | 114 |
| $C_3H_7$ | $C_3H_7$ | H | F | 40 | | | | 107.7 |
| $C_3H_7$ | $C_3H_7$ | F | H | 59 | | | | 108 |
| $C_3H_7$ | $C_5H_{11}$ | H | H | | | | 132.5 | 141.5 |
| $C_3H_7$ | $C_5H_{11}$ | H | F | 28.1–29.7 | | | | 105 |

TABLE 2

Comparative properties of compounds having the formula:

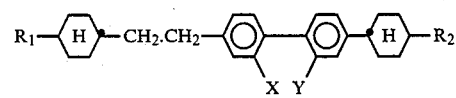

| $R_1$ | $R_2$ | X | Y | K—N | K—S | S—N | N—I |
|---|---|---|---|---|---|---|---|
| $C_3H_7$ | $C_3H_7$ | H | H | | 172 | 201 | 258 |
| $C_3H_7$ | $C_3H_7$ | H | F | 106.8 | | | 244 |

K, S, N and I in Tables 1 and 2 respectively represent solid, smectic, nematic and isotropic phases and K-N etc represent transition temperatures in degrees Celsius. The alkyl chains described in Tables 1 and 2 are all straight. S-S represents a transition from one type of smectic phase to another.

Thus in the compounds without lateral fluorine atoms smectic phases are general and frequently persist above 100° C., whereas such phases in the new class of compound of Formula I are very rare down to room temperature (20° C.). Moreover by making eutectic mixtures of the new compounds the nematic range may be extended down to low temperatures. Thus a mixture of:

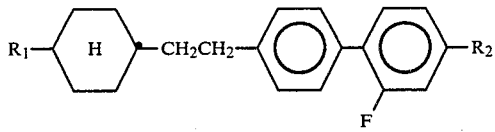

| | | |
|---|---|---|
| $R_1 = \underline{n}\text{-}C_3H_7$ | $R_2 = \underline{n}\text{-}C_3H_7$ | 26% by weight |
| $R_1 = \underline{n}\text{-}C_3H_7$ | $R_2 = \underline{n}\text{-}C_5H_{11}$ | 35% by weight |
| $R_1 = \underline{n}\text{-}C_5H_{11}$ | $R_2 = C_2H_5$ | 39% by weight | referred to in this Specification as Mixture E, has been found to show a nematic phase from the melting point of $-13.5°$ to the clearing point of 103.5° C., without any formation of a smectic phase, and provides an advantageous basis for liquid crystal mixtures that have a low freezing point and will switch fast at low temperatures.

Thus, according to one preferred feature of the invention a nematic or chiral nematic liquid crystal material comprises a mixture of two or more compounds of Formula I. Such a mixture may have an extremely wide nematic or chiral nematic temperature range. The mixture may contain homologues of the same sub-class, eg two or more compounds of Formula Ia.

Alternatively, pairs of compounds may be formed having the same general structure but in different structural isomeric forms with regard to the position of the fluorine, eg in the groups X and Y. In other words one compound may have $X=F$ and $Y=H$ and the other has $Y=F$ and $X=H$ in an otherwise identical structure (eg of Formulae Ia and Ib). Such isomers have similar properties but a mixture of the two can give a very useful depression of melting point.

The property of the lateral fluorine atom in unexpectedly suppressing smectic phases also extends to suppressing the formation of the type of smectic phase, known as an "injected smectic phase", the significance of which is described briefly as follows.

The majority of commercially available electro-optical liquid crystal displays are twisted nematic displays which operate by the twisted nematic effect described below.

If the light intensity output from a twisted nematic display is plotted against the voltage applied the curve obtained is desirably as steep as possible in the region of the so-called optical threshold (which corresponds to the liquid crystal molecules undergoing their most rapid change from the homogeneous configuration to the homeotropic configuration). The steepness of the light output versus voltage curve depends on the liquid crystal material used in the display.

A large proportion of the twisted nematic displays currently available commercially are multiplexed displays, that is to say that individually addressed elements of the display are defined by the region between the inter-section of an electrode of one set on one side of the display panel and an electrode of another set on the other side of the panel, each electrode of each set being shared by all of the elements in a given row or column. Multiplexing allows a greater amount of information to be displayed on a restricted display area and allows the use of a smaller number of electrode connections per number of display elements to be addressed.

In order to produce a liquid crystal material having an adequate multiplexibility for use in a multiplexed twisted nematic display it is generally recognised in the art that the most appropriate way of forming such a material is to mix together two nematic components one of which is formed of one or more compounds having a terminal cyano-group, referred to herein as a "cyano-material", and one of which is formed of one or more compounds having no terminal cyano-group, referred to herein as "non-cyano material". The non-cyano material has a small dielectric anisotropy. The non-cyano material desirably forms at least 30% by weight of the overall mixture of the two components.

The twisted nematic effect operates only when the liquid crystal material is in the nematic phase and not, for example, if the material is in a smectic phase. When a cyano material is mixed with non-cyano material, although the two pure materials may show only nematic liquid crystal phase by themselves, mixtures of them may show unwanted smectic phases known in the art as "injected smectic" phases which appear as areas on the temperature versus composition graph or phase diagram. Injected smectic phases tend to reach peaks on the phase diagram at compositions corresponding to more than 30% by weight of the non-cyano material which are often close to the compositions otherwise preferred for electro-optical operation. It is generally recognised in the art that for a given mixture of a cyano material and a non-cyano material, the smaller the area on the phase diagram taken up by any injected smectic phases and the lower the temperatures at which they occur, the more attractive the given mixture will appear for use in a multiplexed twisted nematic device.

In any event materials for use in commercial twisted nematic effect displays should show a nematic phase down to about $-10°$ C. or beyond. In other words any mixture of a cyano material and a non-cyano material proposed for use in a twisted nematic display should not show injected smectic phases above this temperature.

It is generally recognised by those skilled in the art that the steepness of the light output versus voltage curve specified above can generally be increased by using as liquid crystal materials in a twisted nematic display compositions having components with relatively long-chain terminal groups, such as n-alkyl and n-alkoxy groups, rather than homologues having shorter chain terminal groups. However, it is also generally recognised by those skilled in the art that compounds having relatively long-chain terminal groups generally show a greater tendency to form smectic phases than homologues having relatively short chain terminal groups.

The cyano material in a twisted nematic display preferably comprises compounds of the cyanobiphenyl class, eg 4-n-alkyl-4'-cyanobiphenyls. These compounds are preferred (amongst other reasons) because of the relatively steep light output versus voltage curve they provide. However these compounds are also prone to forming injected smectic phases in mixtures with non-cyano materials.

Thus in order for a given non-cyano material to be of greatest utility in current electro-optical displays it should, amongst other things, be capable of forming mixtures with widely used commercially available cyano materials, particularly those comprising cyanobiphenyl compounds, and its individual compounds should be capable of forming mixtures with the individual compounds of the cyano material with the minimum tendency to give injected smectic phases.

Preferred examples of compounds of Formula I show little tendency to form injected smectic phases and as a consequence are highly suitable for use as "non-cyano" components in mixtures suitable for multiplexed twisted nematic displays also allowing the steepness of the threshold to be improved by the use of longer chained cyano-components. For example, a mixture of 90% by weight of the ternary eutectic mixture Mixture E, of Formula I compounds specified above with 10% by weight of 4-cyano-4'-ethylbiphenyl or of 75% by weight of that ternary eutectic mixture with 25% by weight of trans-4-n-propyl-1-(4-cyanophenyl)-cyclohexane were found to show no injected smectic phases down to −40° C. This property is clearly beneficial in the formation of mixtures required to switch quickly at low temperatures, such as those required by the automobile industry.

In order to minimise the tendency to form smectic phases, particularly injected smectic phases, the overall number of carbon atoms in the two groups $R_1$ and $R_2$ in Formula I, particularly where these groups are n-alkyl groups and particularly in the two groups $R_A$ and $R_B$ in Formulae Ia and Ib, is preferably less than ten; desirably the overall number is between 4 and 8 inclusive. The number of carbon atoms in each of thse individual groups is preferably five or less.

In mixtures of compounds of Formula I, eg mixtures containing compounds of Formula Ia and Ib wherein the terminal groups $R_A$ and $R_B$ are n-alkyl groups, the overall number of carbon atoms in the terminal groups of each compound is preferably in the inclusive range 4 to 8. Preferably, the individual compounds have different overall numbers of carbon atoms in their terminal groups which are all in this range, as in Mixture E specified above.

The compounds of Formula I may be used in applications other than electro-optical applications which are known to be suitable for the use of nematic or chiral nematic liquid crystal compounds. For example, the compounds of Formula I may be incorporated as high clearing point components of temperature sensitive, eg thermochromic, materials, eg for use in the applications described in UK Published Patent Application Nos. 2083244A and 2085585A.

Compounds of Formula I may be prepared by synthetic routes involving procedures which are known per se, the overall route being new. For example, Routes 1 and 2 as follows may be used:

ROUTE 1 where $R_2$ is H, alkyl or alkoxy.

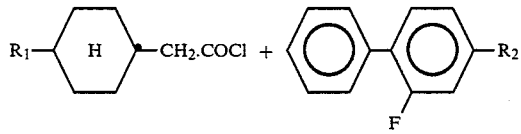

| STEP 1a

-continued
ROUTE 1

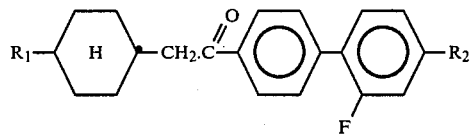

| STEP 1b

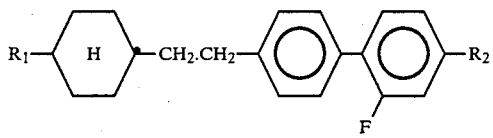

ROUTE 2 where $R_2 = $ 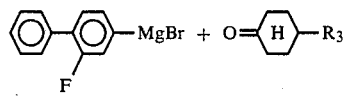

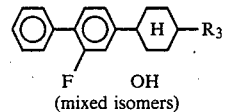

| Step 2a

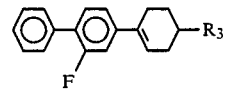
(mixed isomers)

| Step 2b

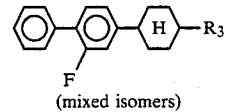

| Step 2c

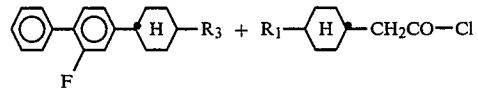
(mixed isomers)

| Step 2d

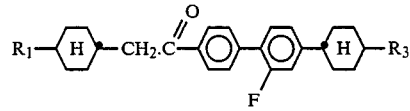

| Step 2e

| Step 2f

-continued
ROUTE 2
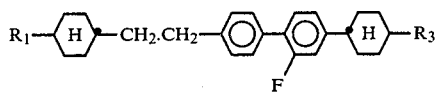
ROUTE 3
where X = F and Y = H:
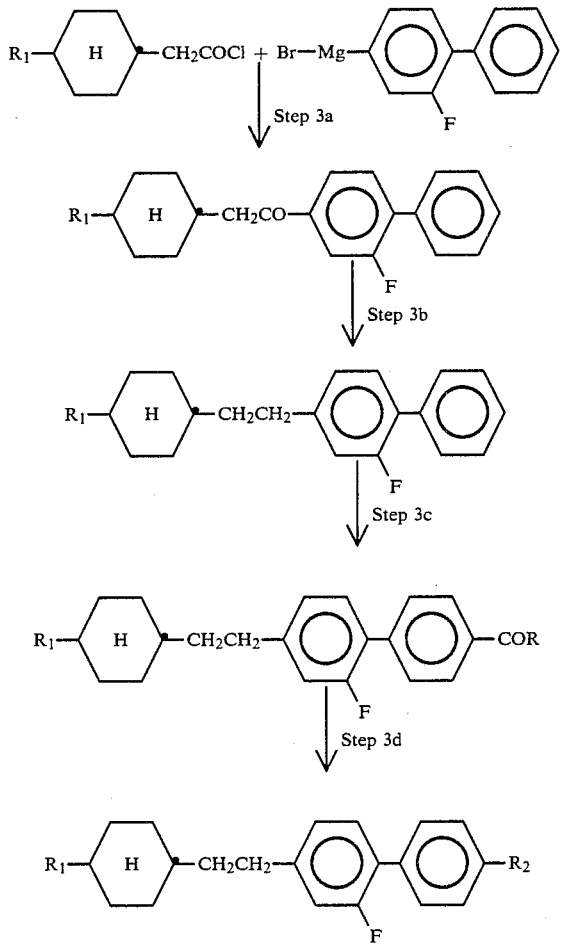
ROUTE 4
where $R_2 = CH_2.CH_2-\bigcirc H\bigcirc-R_1$
$(R_1 = R_2)$ X = H or F, Y = H or F
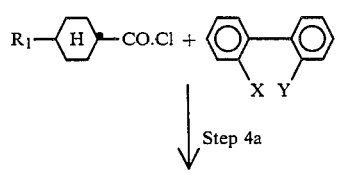
-continued
ROUTE 4
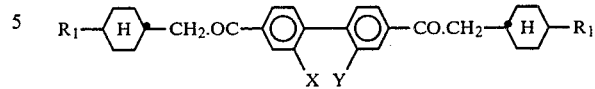
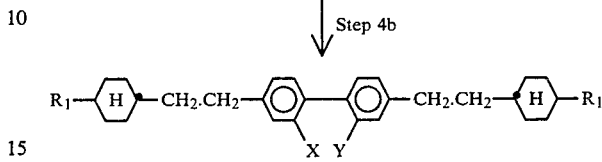
ROUTE 4': for the production of compounds of formula If
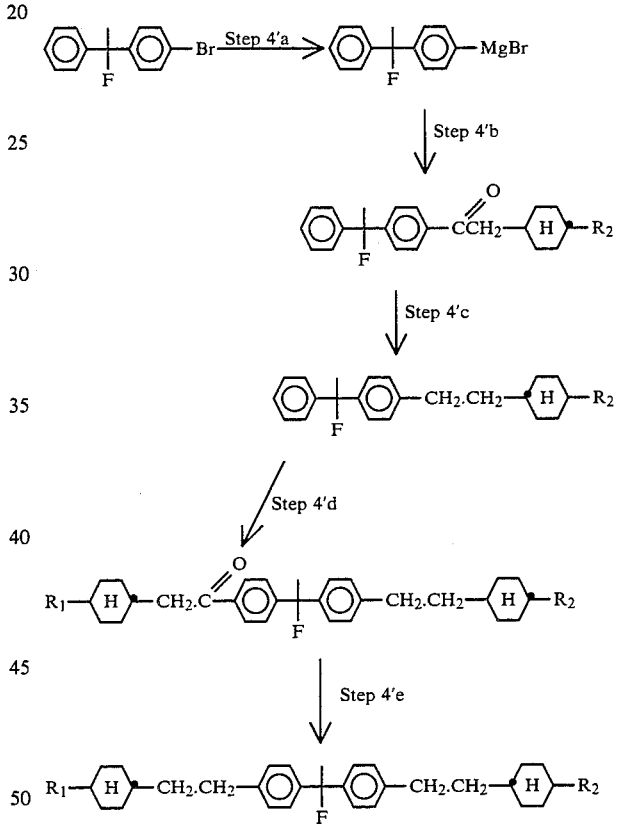
wherein $R_1$ and $R_2$ are the same or different alkyl groups,
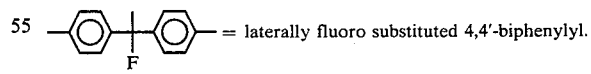 = laterally fluoro substituted 4,4'-biphenylyl.
ROUTE 5
where $R_2 = -\bigcirc-R_2^1$, X = H and Y = F.
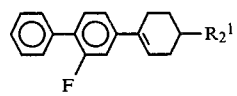

-continued
ROUTE 5

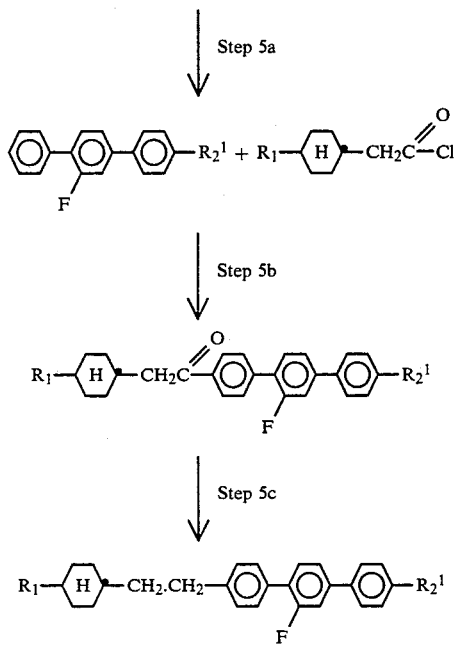

$R_1$ = alkyl, $R_2^1$ = alkyl, alkoxy or hydrogen

ROUTE 6 where $R_2 = $ —⟨O⟩—$R_2'$, X = F, Y = H.

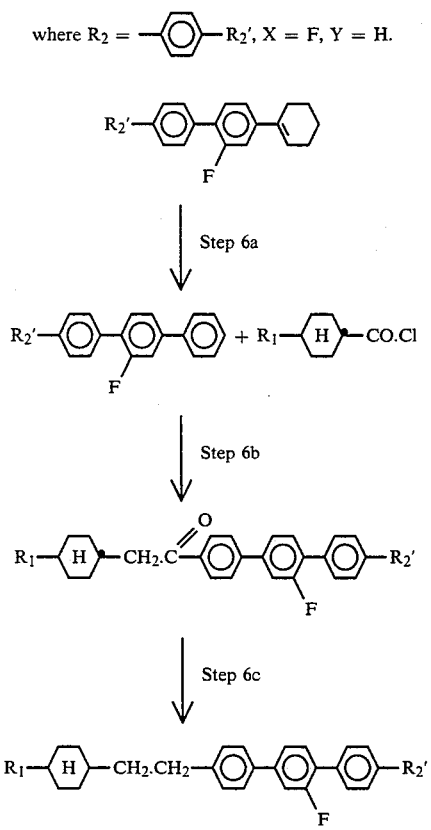

ROUTE 7 where $R_2 = $ —$R_2'$, X = H, Y = H

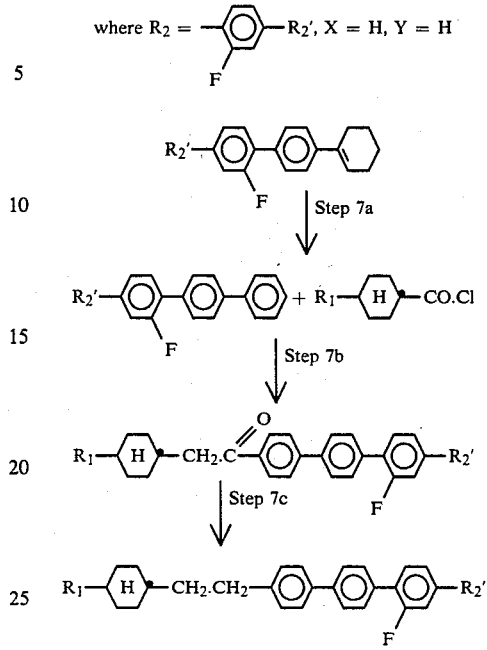

ROUTE 8 where $R_2 = $ —⟨O⟩—$R_2'$; X = F; Y, Z = H

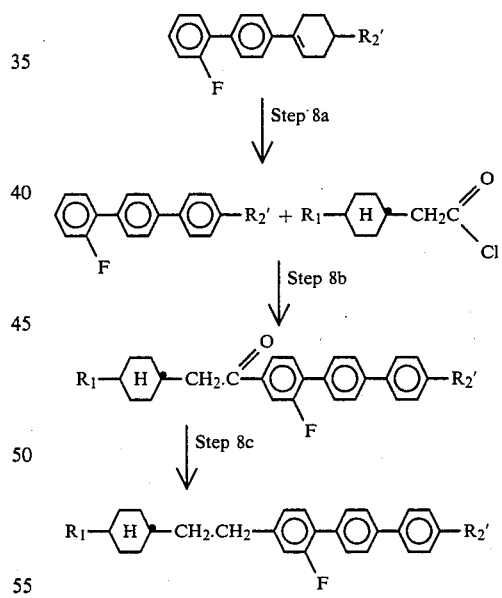

The starting materials for Routes 5, 6, 7 and 8 may be prepared as described in copending UK Patent Application No. 8319849.

The compounds of Formula I have a relatively small dielectric anisotropy and may be added to liquid crystal materials of (greater) positive or negative dielectric anisotropy, known and referred to herein respectively as "positive" or "negative" materials in order to produce a mixture having amongst other things a suitable dielectric anisotropy. As is well known to those skilled in the art the dielectric anisotropy of the liquid crystal material is necessary to give electro-optical operation and its sign (for a given frequency) is chosen according to the kind of electro-optical device in which the material is to be used.

Compounds of reasonably low melting point are preferred as high dielectric anisotropy components. For example, the compounds of the following known classes are suitable as positive materials:

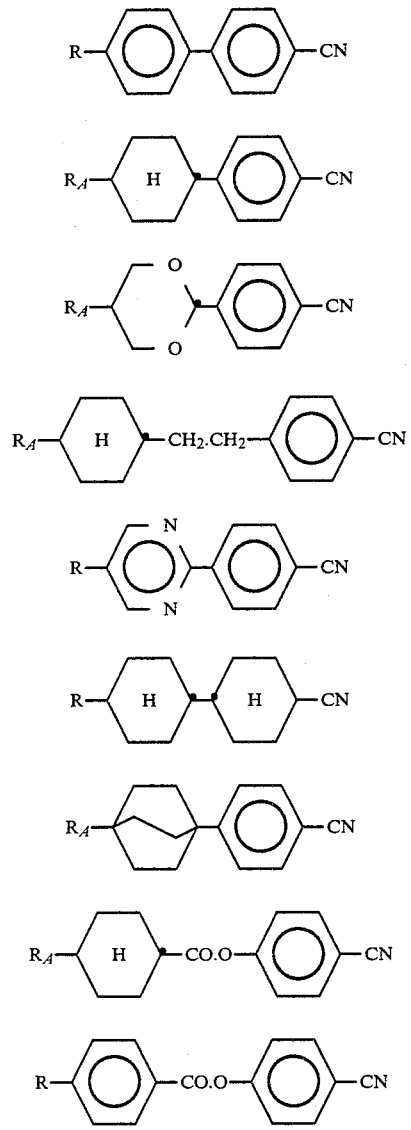

Formula IIa

Formula IIb

Formula IIc

Formula IId

Formula IIe

Formula IIf

Formula IIg

Formula IIh

Formula IIi where each R is independently n-alkyl or n-alkoxy and each $R_A$ is independently n-alkyl.

Alternatively, or additionally, the compounds of Formula I may be added to other small dielectric anisotropy compounds, eg to reduce mixture melting point, viscosity or to improve multiplexibility. The following classes are examples of such other compounds:

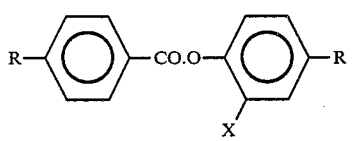

Formula IIIa

-continued

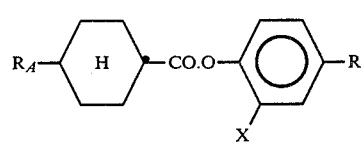

Formula IIIb

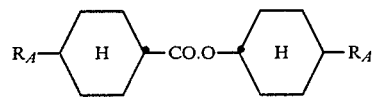

Formula IIIc

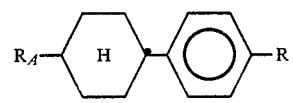

Formula IIId

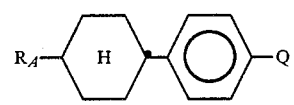

Formula IIIe

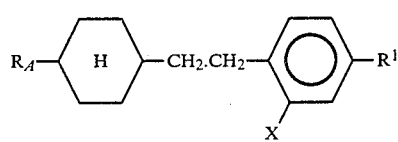

Formula IIIf

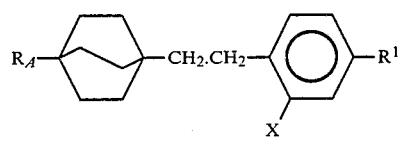

Formula IIIg

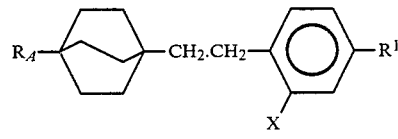

Formula IIIh

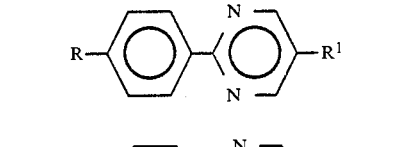

Formula IIIi

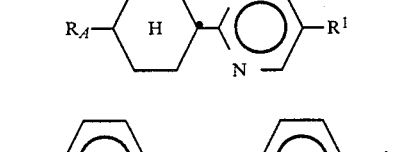

Formula IIIj

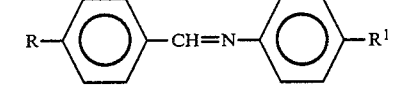

Formula IIIk

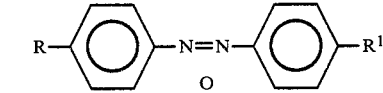

Formula IIIl

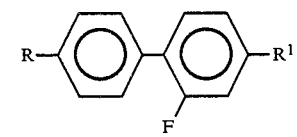

Formula IIIm

Formula IIIn where
each R is independently n-alkyl or n-alkoxy
each $R_A$ is independently n-alkyl
each R' is independently n-alkyl, n-alkoxy or hydrogen
X=H or F
and Q=halogen, eg Cl or F Thus, one or more compounds of Formula I may be added to one or more compounds of Formula IIa to IIi optionally together with one or more compounds of Formula IIIa to IIIn.

Additional high clearing point compounds may be included in such mixtures eg one or more compounds selected from the following classes:

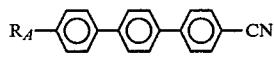
Formula IVa

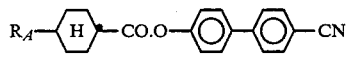
Formula IVb

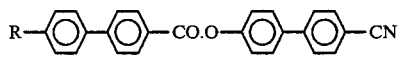
Formula IVc

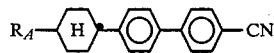
Formula IVd

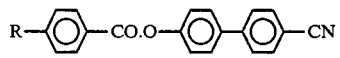
Formula IVe

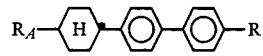
Formula IVf

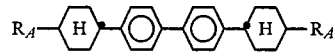
Formula IVg

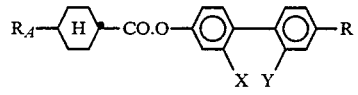
Formula IVh

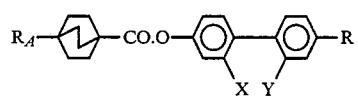
Formula IVi

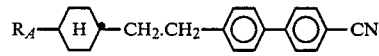
Formula IVj

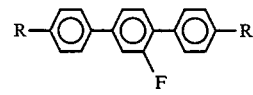
Formula IVk

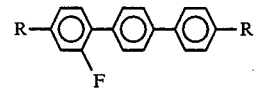
Formula IVl where R, $R_A$, X and Y are as specified above.

Other specific known additives, eg chiral additives, such as

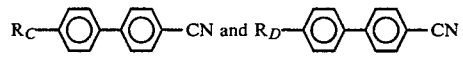

where $R_C$=(+)-2-methylbutyl and $R_D$=(+)-2-methylbutoxy, may be incorporated in the mixture where required.

The liquid crystal material obtained by blending together compounds of Formula I with those of the other classes as specified may be any of the following:

(i) a positive nematic material for use in twisted nematic effect devices including multiplexed devices; an example of such a device is given below;

(ii) a negative material preferably also with a pleochroic dye, for use in Fréedericksz effect devices (negative nematic type) in which the molecular arrangement may be changed from the homeotropic texture (OFF state) to the homogeneous texture (ON state) by an electric field; an example of such a device is given below;

(iii) a positive nematic material, preferably also with a pleochroic dye, for use in Fréedericksz effect devices (positive nematic type) in which the molecular arrangement may be changed from the homogeneous texture (OFF state) to the homeotropic texture (ON state) by an electric field;

(iv) a negative material which is a cholesteric (chiral nematic) of suitable resistivity (about $10^9$ ohm-cm), for use in cholesteric memory mode devices in which the molecular arrangement may be changed from a homogeneous texture (OFF state) to a scattering focal conic texture (ON state) by an electric field;

(v) a strongly negative material which is a cholesteric, preferably together also with a pleochroic dye, for use in cholesteric-to-nematic phase change effect devices (positive contrast type) in which the molecular arrangement may be changed from a weakly scattering, ie clear, surface aligned homeotropic texture (OFF state) to a strongly scattering twisted homogeneous texture (ON state) by an electric field;

(vi) a positive material which is a cholesteric, preferably together also with a pleochroic dye, in cholesteric-to-nematic phase change effect devices (negative contrast type) in which the molecular arrangement may be changed from a scattering focal conic texture (OFF state) to a clear homeotropic texture (ON state) by an electric field;

(vii) a negative nematic material of suitable resistivity (about $10^9$ ohm-cm), in dynamic scattering effect devices in which the molecular arrangement may be changed from a clear homeotropic texture (OFF state) to a turbulent scattering texture (ON state) by an electric field;

(viii) a nematic material in two frequency switching effect devices (which may be twisted nematic effect devices) in which the dielectric anistropy of the material may be changed from (at low frequency) positive (OFF state) to negative (ON state) by the application of a high frequency electric field;

(ix) a material suitable for the device described in copending UK Patent Application No 8317355.

The construction and operation of the above devices and the general kinds of material which are suitable for use in them are themselves known.

Where a liquid crystal material is for use in a twisted nematic effect, cholesteric to nematic phase change effect (negative constrast type) or Fréedericksz effect (positive nematic type) device the material preferably contains:

Component A: one or more compounds of Formula I plus

Component B: one or more compounds of Formula IIa to IIi optionally together with one or more of the following:

Component C: one or more compounds of Formula IIIa to IIIn;

Component D: one or more compounds of Formula IVa to IVl;

Component E: one or more chiral additives.

For the twisted nematic effect and Fréedericksz (positive nematic) effect the following percentages of the various components may be used in the material (the overall sum of the percentages adding to 100%).

Component A: 5 to 95% by weight (typically 5 to 75% by weight)

Component B: 5 to 95% by weight (typically 10 to 50% by weight)

Component C: 0 to 90% by weight (typically 5 to 25% by weight)

Component D: 0 to 30% by weight (typically 0 to 20% by weight)

Component E: 0 to 5% by weight (typically 0 to 1% by weight)

For the phase change (negative contrast type) the following proportions may be used:

Components A to D: in the percentages as specified above;

Component E: 2 to 20% (typically 4 to 5%) by weight.

For the Fréedericksz (positive nematic) and phase change (negative contrast type) effects a pleochroic dye forming from 1.5 to 15% of the overall mixture is preferably added to the liquid crystal material. Suitable dyes are described in published UK Patent Application Nos. 2081736A, 208219A and 2093475A. Typically, each dye compound incorporated forms 1 to 3% by weight of the overall mixture.

Liquid crystal mixtures including compounds of Formula I may be formed in a known way, eg simply by heating the constituent compounds together in the correct weight proportion to form an overall isotropic liquid (eg about 100° C.).

To provide a more general example of a mixture embodying the invention at least one compound according to Formula I above may be mixed together with one or more compounds in any one or more of the following known families for use in one or more of the applications given above (the actual application(s) depending on the mixture's properties):

 i

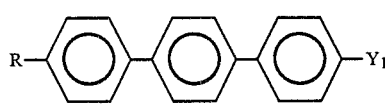 ii

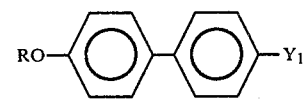 iii

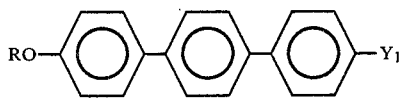 iv

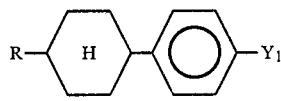 v

 vi

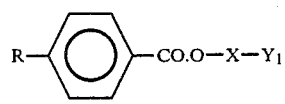 vii

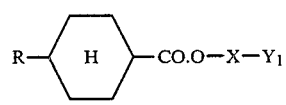 viii

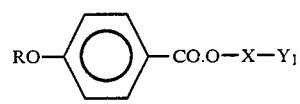 ix

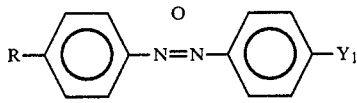 x

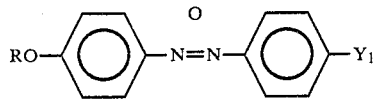 xi

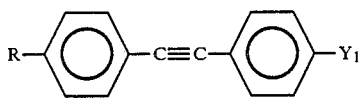 xii

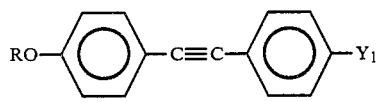 xiii

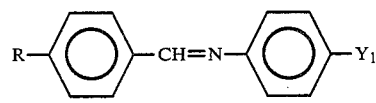 xiv

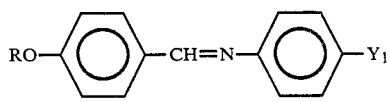 xv

21
-continued

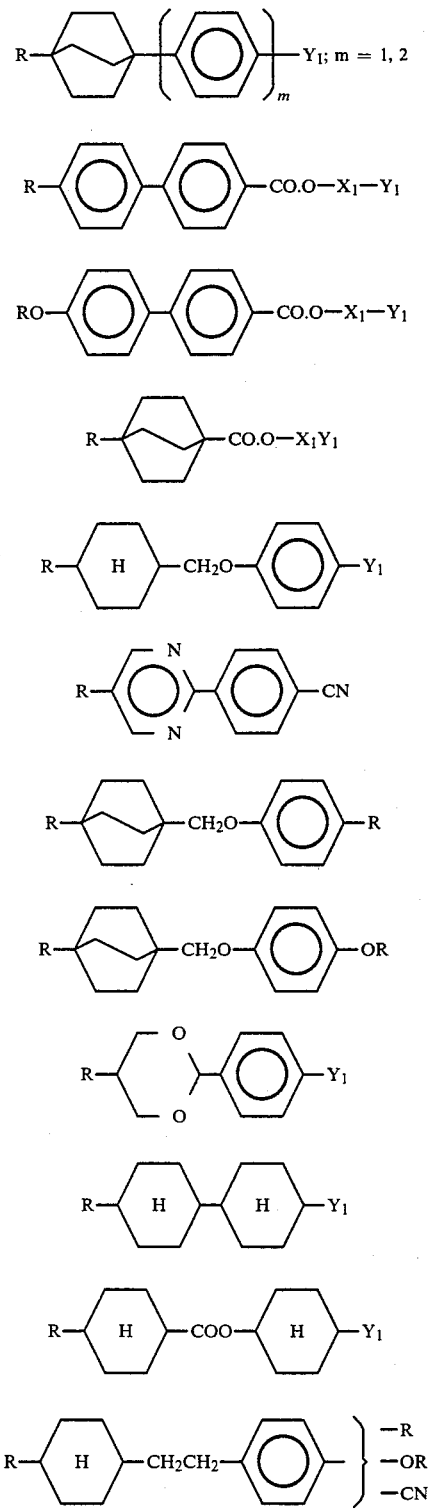

where

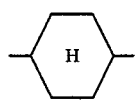

22 xvi is a trans-1,4-disubstituted cyclohexane ring,

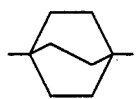

xvii is a 1,4-disubstituted bicyclo(2,2,2)octane ring, X is a 1,4 phenylene group

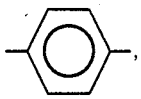

xviii xix a 4,4' biphenylyl group

xx xxi a 2,6 naphthyl group

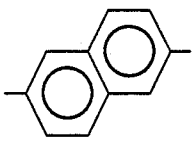

xxii or trans-1,4-disubstituted cyclohexane ring, and $Y_1$ is CN, or R' or halogen or $CO.O-X-Y^1$ where $Y^1$ is CN, or R' or OR'; where R and R' are alkyl groups; or a
xxiii  derivative of one of these wherein H is replaced by a halogen, eg F, in one of the benzene rings.

Preferably, the compound(s) of Formula I comprises between 5 and 95% by weight of the mixture.

xxiv According to the present invention in a second aspect a liquid crystal device includes two dielectric substrates at least one of which is optically transparent, a layer of liquid crystal material sandwiched between the substrates and electrodes on the inner surfaces of the substrates to enable an electric field to be applied across the
xxv layer of liquid crystal material to provide an electro-optic effect therein, characterised in that the liquid crystal material consists of or includes a compound according to Formula I above.

xxvi The device according to the second aspect may be a twisted nematic effect device, which may or may not be operated in a multiplexed fashion, a cholesteric-to-nematic phase change effect device, a Fréedericksz effect device or a two-frequency switching effect de-
xxvii vice, all constructed in a known manner or any of the other devices mentioned above. The various ways in which compounds according to Formula I may be used in these devices are outlined above and will be further apparent to those skilled in the art.

Examples of the preparation and properties of compounds having Formula I will now be given. In these Examples the following symbols are used:

mp=melting point
K-N=crystal to nematic liquid crystal transition temperature
N-I=nematic to isotropic liquid transition temperature bp=boiling point
S=smectic
$S_A$=smectic A
S-N=smectic to nematic transition temperature
K-S=crystalline solid to smectic transition temperature
Ch-I=cholesteric (chiral nematic) to isotropic liquid transition temperature;
K-Ch=crystalline solid to cholesteric transition temperature
S-Ch=smectic to cholesteric transition temperature
Δn=birefringence measured at 589.6 nm at 20° C.
η=extrapolated nematic viscosity at 20° C. measured in solution with the material ZLI 1132 (available from E Merck Co.)
glc=gas liquid chromatography

EXAMPLE 1

The preparation of 1-(trans-4-n-pentylcyclohexyl)-2-(4-ethyl-2-fluoro-4-biphenylyl)-ethane by Route 1 given above.

Step 1a1

The preparation of 4-(trans-4-n-pentylcyclohexylacetyl)-2'-fluoro-4'-ethyl-biphenyl by Friedel Crafts acylation:

4-Ethyl-2-fluorobiphenyl (13.0 gram) was added in one portion to a stirred suspension of aluminium trichloride (9.54 gram) in dichloromethane (30 ml), followed by a solution of trans-4-n-pentylcyclohexyl acetyl chloride (15 gram) in dichloromethane (30 ml), added dropwise over 30 minutes. After stirring at room temperature for 3½ hours, the reaction mixture was poured onto ice (250 gram) and hydrochloric acid (25 ml) and the product was extracted with 350 ml and 250 ml portions of petroleum ether (boiling point 60°-80° C.). The combined extracts were washed with water (150 ml), dried over anhydrous sodium sulphate and evaporated to dryness. The residue (26.8 gram) was crystallised from industrial methylated spirits at 0° C. to give 13.2 gram (51.5% yield) 4-(trans-4-n-pentylcyclohexylacetyl)-2'-fluoro-4'-ethylbiphenyl, melting point 72°-73° C.

The following homologues of the product of Step 1a1 listed in Table 3 were prepared in an identical manner from homologous starting materials:

TABLE 3

Compounds of the formula:

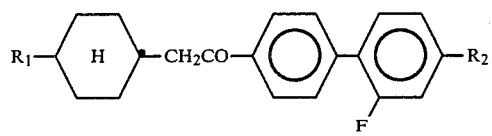

| $R_1$ | $R_2$ | Yield | mp or K—N | N—I (°C.) |
|---|---|---|---|---|
| $C_2H_5$ | $C_2H_5$ | 89.8% | 77 5-78.3 | |
| $C_2H_5$ | n-$C_3H_7$ | 76.3% | 54-56 | |
| $C_2H_5$ | n-$C_4H_9$ | 87% | 65.8-66.7 | |
| n-$C_3H_7$ | $C_2H_5$ | 74% | 76-78 | |
| n-$C_3H_7$ | n-$C_3H_7$ | 86% | 84-86 | 91-93 |
| n-$C_3H_7$ | n-$C_4H_9$ | 82% | 70-72.5 | 85.1-86.7 |
| n-$C_3H_7$ | n-$C_5H_{11}$ | 86% | 66.5-68 | 92-94 |
| n-$C_4H_9$ | $CH_3$ | 81% | 74.5-76.5 | 87.4-88.1 |
| n-$C_4H_9$ | $C_2H_5$ | 84% | 70-73 | 77 |
| n-$C_4H_9$ | n-$C_3H_7$ | 83% | 72 | 91.5 |
| n-$C_4H_9$ | n-$C_4H_9$ | 78% | 69.6-71 | 87.1-87.8 |
| n-$C_5H_{11}$ | H | 66% | 111-114 | |

Step 1b1

The preparation of 1-(trans-4-n-pentylcyclohexyl)-2-(4'-ethyl-2'-fluoro-4-biphenylyl)-ethane by Huang Minlon reduction:

The ketone prepared in Step 1a1 (13.0 gram), 99% hydrazine hydrate (13 ml), potassium hydroxide (7 gram) and digol (100 ml) were heated with stirring under a reflux condenser at 120°-125° for 4 hours, after which the temperature was raised to 175° by distillation of the excess hydrazine hydrate. The mixture was heated under reflux for 16 hours, cooled and poured onto 500 gram ice water. The organic product was extracted with petroleum ether (bp 60°-80°: 2×250 ml), and the extract washed with water and dried over anhydrous sodium sulphate, and evaporated to give a yellow oil (13.8 gram). This was dissolved in petroleum spirit (bp 60°-80° C.) (60 ml) and adsorbed onto a column of basic alumina (40 gram) over silica gel (28 gram). Elution with petroleum spirit (550 ml) gave the product as a nematic oil (10.9 gram) which was crystallised from industrial methylated spirits (30 ml) at −25° C.

1-(Trans-4-n-pentylcyclohexyl)-2-(4'-ethyl-2'-fluoro-4-biphenylyl)-ethane formed a colourless crystalline solid (8.3 grams—yield 67%) with K-N (melting point), N-I (clearing point) 103.50° C.: its viscosity and birefringence at 589.6 nm both measured at 20° C. on the supercooled liquid were 32.6 cSt and 0.145 respectively.

The following homologues of the product of Step 1b1 listed in Table 4 were prepared by Huang Minlon reduction of the appropriate ketone in the manner described in Step 1b1.

TABLE 4

Compounds of the formula:

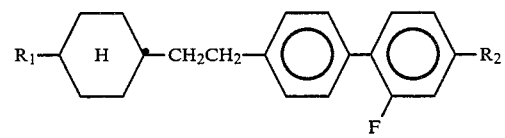

| $R_1$ | $R_2$ | Yield | K—N | S—N or monotropic S phase | N—I (°C.) | Δn | η (cst) |
|---|---|---|---|---|---|---|---|
| $C_2H_5$ | $C_2H_5$ | 84% | 14-14.8° | | 65.7-66.2 | 0.1395 | 22.5 |

TABLE 4-continued

Compounds of the formula:

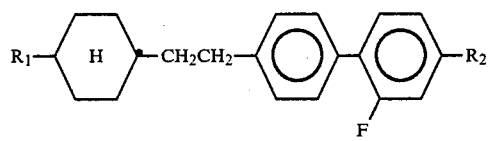

| R₁ | R₂ | Yield | K—N | S—N or monotropic S phase | N—I (°C.) | Δn | η (cst) |
|---|---|---|---|---|---|---|---|
| C₂H₅ | n-C₃H₇ | 45% | 21.3° | | 78.3–78.5 | 0.1461 | 24 |
| C₂H₅ | n-C₄H₉ | 80% | −2° | | 69–70.2 | 0.1353 | 26 |
| n-C₃H₇ | C₂H₅ | 83% | 27–27.5° | | 96.8–97.1 | | 19 |
| n-C₃H₇ | n-C₃H₇ | 78% | 39.8–40.5° | | 107.6–107.8 | | 23 |
| n-C₃H₇ | n-C₄H₉ | 60% | 13.1–13.6° | [2°] | 96.4–96.8 | 0.1432 | 22.5 |
| n-C₃H₇ | n-C₅H₁₁ | 51% | 28.1–29.7° | | 105.1 | | 24.5 |
| n-C₄H₉ | CH₃ | 63% | 27–27.7° | | 104.5–105 | | 28 |
| n-C₄H₉ | C₂H₅ | 60% | 25.4° | [3.5°] | 93–93.7 | 0.1395 | 22 |
| n-C₄H₉ | n-C₃H₇ | 70% | 23.9–24.6° | | 103.1 | 0.1452 | 25 |
| n-C₄H₉ | n-C₄H₉ | 66.5% | | 24.2–24.5 | 94.2–94.5 | | 26.5 |
| n-C₅H₁₁ | H | 85% | 42.5–44.1° | | 49.6 | | 30 |

4-Ethyl-2-fluoro biphenyl, which is one of the starting materials used in Step 1a1, was prepared as follows:

4-Acetyl-2-fluorobiphenyl (150 gram), 99% hydrazine hydrate (150 ml), potassium hydroxide (105 gram), digol (900 ml) and xylene (150 ml) were heated at 125° C. for 16 hours with stirring, after which the xylene and excess hydrazine hydrate were distilled until the internal temperature reached 165° C. The mixture was heated under reflux for three hours, cooled to 40° and poured into 5 liters of water. The product was extracted with petroleum ether (bp 60°–80°, 2×2 liter), the extract washed with water, dried over anhydrous sodium sulphate and evaporated. 4-Ethyl-2-fluorobiphenyl (95 gram, 68% theory) formed a colourless oil bp 130°/0.8 mm. Other 4-Alkyl-2-fluorobiphenyls were prepared by reaction of 2-fluoro-4-biphenylyl magnesium bromides with n-alkyl bromides and were colourless oils with the following properties listed in Table 5.

TABLE 5

Properties of 4-alkyl-2-fluorobiphenyls.

| Alkyl group | Yield | bp (°C.) |
|---|---|---|
| Methyl | 58% | 120° at 6 torr |
| n-Propyl | 61.5% | 108° at 0.15 torr |
| n-Butyl | 65% | 106° at 7 torr |
| n-Pentyl | 69% | 152° at 0.3 torr |

The following mixtures incorporating the product of Step 1b1 illustrate the usefulness of that compound.

(a) with cyanobiphenyl components. The commercially available liquid crystal material E7, supplied by BDH Chemicals Ltd, which contains:

51% 4-cyano-4′-n-pentyl biphenyl
25% 4-cyano-4′-n-heptylbiphenyl
16% 4-cyano-4′-n-octyloxybiphenyl
8% 4-cyano-4″-n-pentyl-p-terphenyl was added to the product of Step 1b1 here designated as Compound A. In the resulting solution (Mixture A) Compound A formed 25% by weight of the weight of E7 present (ie 20% by weight of Compound A and 80% by weight of E7 overall). Various properties were measured for the resulting solution and these were compared with the corresponding properties for E7 alone. These comparative properties, which are listed in Table 1, are denoted in that Table by the abbreviations specified above together with:

T_F=a temperature at which the liquid crystalline material may be kept for 72 hours without freezing

TABLE 6

Comparative properties of E7 with and without Compound A.

| Property measured | Result for E7 without Compound A | Result for E7 with Compound A (20% Compound A + 80% E7) |
|---|---|---|
| N-I (°C.) | 60.5 | 69.5–71.0 |
| T_F (°C.) | −10 | −25 |
| Δn | 0.225 | 0.210 |
| η (cSt) | 40.0 | 37.5 |

All four properties listed in Table 1 are improved by the addition of Compound A to E7. Furthermore, the mixture of E7 plus Compound A as specified above showed (like E7) no smectic phase at temperatures down to −20° C.

(b) With PCH components. A mixture was formed using 20% by weight of Compound A with 80% of the commercially available ZLI 1132 (supplied by E Merck Co.) of the following composition by weight (Mixture B).

24% trans-4-n-propyl-1-(4-cyanophenyl)cyclohexane
36% trans-4-n-pentyl-1-(4-cyanophenyl)cyclohexane
25% trans-4-n-heptyl-1-(4-cyanophenyl)cyclohexane
15% trans-4-n-pentyl-1-(4′-cyano-4-biphenylyl)cyclohexane Comparative properties for ZLI 1132 with and without Compound A were measured in the same way as specified above. These comparative properties are listed in Table 2 as follows:

TABLE 7

Comparative properties of ZLI 1132 with and without Compound A.

| Property measured | Result for ZLI 1132 without Compound A | Result for ZLI 1132 with Compound A (20% Compound A 80% ZLI 1132) |
|---|---|---|
| N-I (°C.) | 71.3–74 | 79.5–82.5 |
| T_F (°C.) | −6 | −25 |
| Δn | 0.140 | 0.140 |

TABLE 7-continued

Comparative properties of ZLI 1132 with and without Compound A.

| Property measured | Result for ZLI 1132 without Compound A | Result for ZLI 1132 with Compound A (20% Compound A 80% ZLI 1132) |
|---|---|---|
| η (cSt) | 27.5 | 26.5 |

As seen in Table 7 three of the properties of ZLI 1132 are improved by the addition of Compound A and the fourth property, birefringence, is unchanged.

In addition, the mixture of ZLI 1132 plus Compound A specified above showed no smectic phase down to $-20°$ C.

(c) A fast-switching broad range mixture: A mixture, Mixture C, was prepared with the following components by weight.

9.95% 4-cyano-4'-ethylbiphenyl
4.98% Trans-4-n-propyl-1-(4-cyanophenyl)-cyclohexane
4.98% 4-cyano-4'-n-propylbiphenyl
6.96% 1-(Trans-4-n-Propylcyclohexyl)-2-(4'-cyano-4-biphenyl)-ethane
2.98% 4'-Cyano-4-biphenylyl 4'-n-heptyl-4-biphenyl-carboxylate
18.11% 1-(Trans-4-n-propylcyclohexyl)-2-(4'-n-propyl-2'-fluoro-4-biphenylyl)-ethane
24.38% 1-(Trans-4-n-propylcyclohexyl)-2-(4'-n-pentyl-2'-flouro-4-biphenylyl)-ethane
27.17% 1-(Trans-4-n-pentylcyclohexyl)-2-(4'-ethane-2'-fluoro-4-biphenylyl)-ethane
0.48% (+)-4-Cyano-4'-(2-methylbutyl)-biphenyl and was found to have the following properties:

| K—N: | Not frozen after storing for 1 month at $-35°$ C. |
|---|---|
| N—I: | 102° C. |
| Birefringence: | 0.1735 at 589.6 nm at 20° C. |
| Threshold voltage: | 2.85 volts |
| $T_{on}$ 400 ms | measured in a twisted nematic electro-optical cell having a liquid crystal layer thickness of 7 μm and driven at 8 volts RMS at $-20°$ C. |
| $T_{off}$ 540 ms | |

$T_{on}$ and $T_{off}$ are respectively the times required to switch the cell ON and OFF respectively and are measured between 10 and 90% of the cell transmission.

(d) Mixtures with minimal temperature variation of the threshold voltage.

The following mixtures listed in Table 8 were prepared and their properties as stated were measured in a twisted nematic electro-optical cell having a liquid crystal layer thickness of 7 μm.

TABLE 8

| | Liquid Crystal Mixtures | | | |
|---|---|---|---|---|
| Mixture Name | Positive Component (% by weight) | Ternary eutectic (% by weight) | Threshold voltage, V (Volts) | $-\frac{1}{V} \cdot \frac{dV_{90}}{dT_{0-50°}}$ (mV % °C.$^{-1}$) |
| D1 | 5% K6 | 95% E | 5.17 | 0.11 |
| D2 | 10% K6 | 90% E | 3.67 | 0.15 |
| D3 | 5% PCH3 | 95% E | 5.56 | 0.13 |
| D4 | 10% PCH3 | 90% E | 4.09 | 0.16 |

In Table 8 E represents the ternary eutectic mixture of Formula I compounds specified above, K6 represents 4-cyano-4'-n-ethylbiphenyl obtained from BDH Chemicals Ltd and PCH3 represents trans-4n-propyl-(4-cyanophenyl)cyclohexane obtained from E Merck Co., Darmstadt.

The parameter $-1./V$ (dV/dT$_{0°-50°}$ C.) is a measure of the variation of threshold voltage with temperature over the range 0° C. to 50° C., V being the threshold voltage at 20° C. (required to give 90% transmission through the cell) and T being temperature.

EXAMPLE 2

The preparation of 1-(trans-4-n-propylcyclohexyl)-2-[4'-(4-trans-n-propylcyclohexyl)-2'-fluoro-4-biphenylyl]-ethane by Route 2 specified above.

Step 2a1:
1-2-(Fluoro-4-biphenylyl)-4-n-propylcyclohexan-1-ol

A few ml of a solution of 4-bromo-2-fluorobiphenyl (50 gram) in diethyl ether (150 ml) was added to magnesium turnings (5.3 gram) and diethyl ether (25 ml) under nitrogen. A crystal of iodine was added and reaction was initiated by warming. The remainder of the solution of 4-bromo-3-fluorobiphenyl was then added at a rate fast enough to sustain vigorous refluxing. After boiling for 1 hour, the solution of the Grignard reagent was cooled to 20° C. and then a solution of 4-n-propylcyclohexanone (27.9 gram) in diethyl ether (75 ml) was added over 30 minutes. After stirring for 1 hour, the mixture was poured onto 15% hydrochloric acid (2 liter) and the product extracted with ether (2×300 ml). The combined extracts were washed with water, dried and evaporated. The residue was crystallised from petroleum ether (b.p. 60°–80°, 120 ml) to give 1-(2-fluoro-4-biphenylyl)-4-propyl cyclohexane-1-ol as pale yellow crystals, m.p. 45°-72° (37.2 gram: 61.2% theory) (isomer ratio by glc 60.6: 39.4).

Step 2b1:
1-(2-Fluoro-4-biphenylyl)-4-n-propylcyclohex-1-ene

Phosphorous pentoxide (40 grams) was added to a cooled and stirred solution of the product from Step 2a1 (35.5 gram) in toluene (500 ml). The mixture was kept at room temperature for 4 hours and then added to 1 liter water. After stirring for 30 minutes, the organic layer was separated and the aqueous layer re-extracted with toluene (300 ml). The combined extracts were washed neutral, dried and evaporated to dryness under vacuum. The yellow residue was recrystallised from ethanol (200 ml) at 5° C. to give 29.3 gram (88% theory) 1-(2-fluoro-4-biphenyl)-4-n-propyl-cyclohex-1-ene mp. 60.1–60.4° C. The product was found to be 99.5% pure by glc.

Step 2c1: 2-Fluoro-4-(4-n-propylcyclohexyl)-biphenyl (mixed isomers)

The corresponding cyclohexane from step 2b1 (7 gram), 5% palladium on charcoal (0.7 gram), and ethanol were stirred in an atmosphere of hydrogen at 40° C. until uptake of hydrogen ceased. The catalyst was filtered off and the solvent evaporated to leave the product as a mixture of isomers determined by glc to be 64.5% cis- and 34.5: trans-.

A solution of the mixed isomers (9 gram) prepared as above in dimethyl formamide (50 ml) was aded to a suspension of sodium hydride (2.4 gram) in dimethylformamide (50 ml). The mixture was heated and stirred at 60° C. for 20 hours and then added firstly to ethanol (100 ml) and then to water (1 liter). The product was extracted with petroleum ether (bp 60°–80° C. 2×200 ml) washed with water, dried and evaporated to dryness. The residue (9.1 gram) now consisted of 83% trans isomer and was purified by crystallisation from ethanol (30 ml) at 5° C. to give the trans- product (5.6 gram, 99.5% pure by glc), mp 69°-70° C.

Step 2d1:
4-(Trans-4-n-propylcyclohexylacetyl)-2'-fluoro-4'-(trans-4-n-propylcyclohexyl)-biphenyl The product from Step 2c1 was reacted with trans-4-n-propylcyclohexyl acetyl chloride as described in Step 1a1. 4-(Trans-4-n-propylcyclohexylacetyl)-2'-fluoro-4'-trans-4-n-propylcyclohexyl)-biphenyl crystallised from petroleum ether (bpt. 60°-80°) (63% yield). The product had the following properties:

$K-S_A=90°$; $S_A-N=179°-180°$; $N-I=220°-223°$. It was found to be 99.8% oure by glc.

The product of Step 2d1, and other examples of compounds of formula Ik which may be prepared analogously, are summarised in Table 2 as follows:

TABLE 2
Compounds of formula:

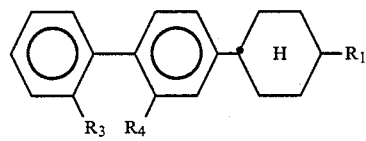

| $R_1$ | $R_3$ | $R_4$ | $R_1$ | $R_3$ | $R_4$ | $R_1$ | $R_3$ | $R_4$ |
|---|---|---|---|---|---|---|---|---|
| $CH_3$ | H | F | $n-C_5H_{11}$ | H | F | $n-C_9H_{19}$ | H | F |
| $CH_3$ | F | H | $n-C_5H_{11}$ | F | H | $n-C_9H_{19}$ | F | H |
| $C_2H_5$ | H | F | $n-C_6H_{13}$ | H | F | $n-C_{10}H_{21}$ | H | F |
| $C_2H_5$ | F | H | $n-C_6H_{13}$ | F | H | $n-C_{10}H_{21}$ | F | H |
| $n-C_3H_7$ | H | F | $n-C_7H_{15}$ | H | F | $n-C_{11}H_{23}$ | H | F |
| $n-C_3H_7$ | F | H | $n-C_7H_{15}$ | F | H | $n-C_{11}H_{23}$ | F | H |
| $n-C_4H_9$ | H | F | $n-C_8H_{17}$ | H | F | $n-C_{12}H_{25}$ | H | F |
| $n-C_4H_9$ | F | H | $n-C_8H_{17}$ | F | H | $n-C_{12}H_{25}$ | F | H |

Step 2e1:
4-(Trans-4-n-propulcyclohexylacetyl)-2'-fluoro-4'-(trans-4-n-propylcyclohexyl)-biphenyl The product from Step 2d1 (5 gram) and trans-4-n-propylcyclohexyl acetyl chloride (3.42 gram) in dichloromethane (30 ml) were added over a period of 40 minutes to a stirred suspension of aluminium trichloride in dichlormethane (15 ml) at 10° C. After allowing the temperature to reach room temperature (20° C.) the mixture was stirred for 4 hours. It was then poured onto water (150 ml). Subsequently, the product was extracted with petroleum spirit (bp 60°-80° C; 2×200 ml). This was washed with water, dried over anhydrous sodium sulphate and evaporated to dryness to give 7.7 grams of a yellow solid. The pure product was recrystallised from petroleum spirit at 10° C. The yield was 4.9 gram (63%) and the purity 99.8%.

Step 2f1:
1-(Trans-4-n-propylcyclohexyl)-2-[2'-fluoro-4'-(trans-4-n-propylcyclyhexyl)-4-biphenyl]-ethane The ketone prepared to Step 2a1 (4.8 gram), 99% hydrazine hydrate (5 ml), potassium hydroxide (2 gram) and digol (35 ml) were heated with stirring under a reflux condenser at 120°-125° C. for 5 hours, after which the temperature was raised to 180° C. by distillation of the excess hydrazine hydrate. The mixture was heated under reflux for 20 hours, cooled and poured onto 300 ml water. The organic product was extracted with a 4:1 solution of petroleum spirit (bp 60°-80°)/dichloromethane 2×(20 ml), and the extract washed with water and dried over anhydrous sodium sulphate, and evaporated to give 4.6 gram of solid. This was dissolved in petroleum spirit (by 60°-80° C.) (60 ml) and absorbed onto a column of basic alumina (10 gram) over silica gel (5 gram). Elution with petroleum spirit (150 ml) gave 4.3 grams of the crude product. Following recrystallisation from petroleum spirit 3.4 gram of the product (found to be 99.9% pure) was obtained in 73% yield and showed $K-N=106°-108°$ C. and $N-I=244°$ C.

EXAMPLE 3

The preparation of 1-(trans-4-n-propylcyclohexyl)-2-(2-fluoro-4'-n-propyl-4-biphenylyl)-ethane by Route 3 above

Step 3a1:
2-Fluoro-4-(trans-4-n-propylcyclohexyl)biphenyl

A solution of 4-bromo-2-fluorobiphenyl (38.1 gram) in tetrahydrofuran (60 ml) was added over 20 minutes to magnesium turnings (4 gram) suspended in tetrahydrofuran (20 ml), reaction being initiated by adding a crystal of iodine and warming as usual. This Grignard reagent was now added to a solution of trans-4-propylcyclohexylacetyl chloride (40 gram) and cuprous chloride (0.4 gram) in tetrahydrofuran (200 ml) with stirring at −60° C. over 90 minutes. After allowing to warm to room temperature over two hours, the mixture was decomposed with water and the product extracted with petroleum ether (bpt. 60°-80°). The crude material was recrystallized twice from ethanol at 5° C. to give the product (20.6 gram, 40% theory), m.p. 96.5°-97.3° C., which was found to be 99.6 pure by glc.

Step 3b1:
1-(2-fluoro-4-biphenylyl)-2-(trans-4-n-propylcyclohexyl)-ethane

The ketone produced in Step 3a was reduced as described in Step 1b1 to give the product in 71% yield, 99.8% pure by glc. The product was found to have mp=46.5°-48° (N-I [37°-39.8°]).

Step 3c1:
1-(2-Fluoro-4'-propionyl-4-biphenylyl)-2-(trans-4-n-propylcyclohexyl)-ethane The 4'propionyl- group was introduced into the product of Step 3b1 by the technique for carrying out Friedel-Craft reactions described in Step 1a1. The desired product was obtained in 90% yield, 99.7% pure by glc. The product showed the following properties:
$K-N=74.4°-74.8°$; $N-I=165.4°-165.8°$ C.

Step 3d1:
1-(2-Fluoro-4'-n-propyl-4-biphenylyl)-2-(trans-4-n-propylcyclohexyl)-ethane The ketone produced by Step 3c1 was reduced by the Huang-Minlon procedure described in step 1b1 to give the product in 30% yield, 99.8% pure as determined by glc. The product had $K-N=59°$, $N-I=108°$.

The following homologues were prepared by identical sequences of reactions.

TABLE 9

Compounds having the formula:

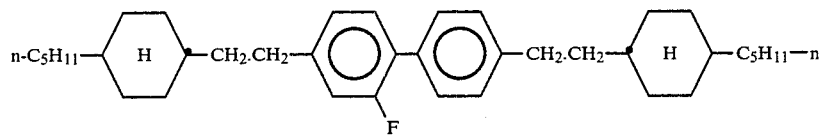

| R₁ | R₂ | K—N (°C.) | monotropic smectic phase | N—I (°C.) | Extrapolated nematic viscosity at 20° C. (cSt) |
|---|---|---|---|---|---|
| C₂H₅ | n-C₃H₇ | 34 | | 80 | 25.5 |
| n C₃H₇ | C₂H₅ | 34 | [15] | 97 | |
| n C₅H₁₁ | H | 39 | | 53 | |

EXAMPLE 4

The preparation of the compound of formula:

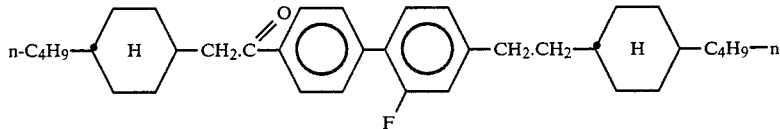

by Route 4 given above.

Step 4a1

This Friedel Crafts acrylation was carried out as in Step 1a1 except that 2-fluorobiphenyl was used in place of 4-ethyl-2-fluorobiphenyl and that the molar amount of aluminum trichloride in dichloromethane present was doubled as was the amount of trans-4-n-pentylcyclohexylacetyl chloride.

Step 4b1

This Huang Minlon reduction was carried out in essentially the same way as Step 1b1 above.

Compounds of Formula If containing other alkyl groups may be made in an analogous way.

EXAMPLE 4'

The preparation of the compound of formula

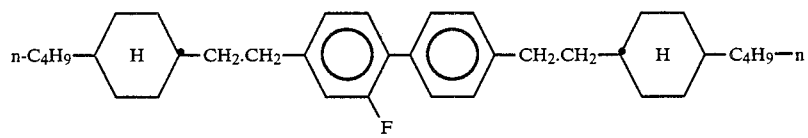

by Route 4' above. Steps 4'a1 to 4'e1 as follows are specific examples of Steps 4'a to 4'e respectively.

Step 4'a1: Production of the Grignard reagent

This step was carried out in a manner similar to the production of the Grignard reagent is Step 1a1 above, 4-bromo-2-fluorobiphenyl as starting material.

Step 4'b1

This step was carried out by the conventional reaction of trans-4-n-butyl cyclohexyl acetyl chloride together with the Grignard reagent produced in Step 4'a1 in the presence of tetrahydrofuran at a temperature of −78° C. in the manner described by F Sato, M Inoue, K Oguro and M Sato in Tetrahedron Letters (1979) pages 4303 to 4306.

Step 4c1: Reduction

This step was carried out in a manner similar to the reduction in Step 1b1 above. The product, of formula:

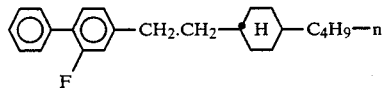

showed the following properties: C-I=44° C. N-I=(36.6° C.).

Step 4'd1: Friedel Crafts acylation

The step was carried out in a manner similar to Step 1a1 above. The product, of formula:

showed the properties=C-S=110° C; S-N=185.7° C. and N-I=190.1° C.

Step 4'e1: Reduction

This step was carried out in a manner similar to step 1b1 above. The product was of formula:

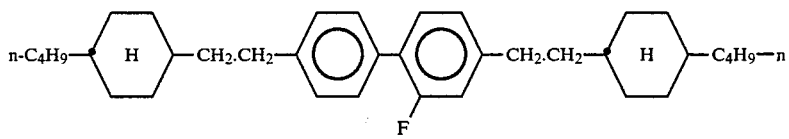

Compounds of Formula If containing other alkyl groups may be made in an analogous way.

The compounds which may be made in the manner described in Examples 1 to 4 and 4' are summarized in Tables 10 to 13 respectively, as follows:

TABLE 10
Compounds of the formula:

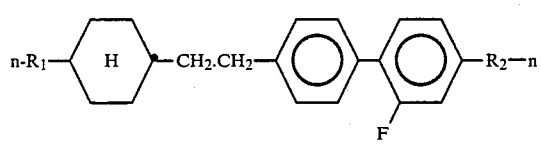

| $R_1$ | $R_2$ |
|---|---|
| $C_mH_{2m+1}$ | $C_pH_{2p+1}$ |
| $C_mH_{2m+1}$ | $OC_pH_{2p+1}$ |
| $C_mH_{2m+1}$ | H | where
m includes all integer values from 0 to 12 inclusive and
p includes all integer values from 1 to 12 inclusive.

TABLE 11
Compounds of the formula:

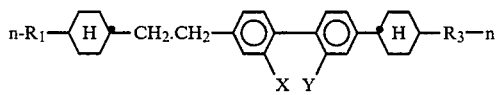

| $R_1$ | $R_3$ | X | Y |
|---|---|---|---|
| $n\text{-}C_mH_{2m+1}$ | $n\text{-}C_pH_{2p+1}$ | H | F |
| $n\text{-}C_mH_{2m+1}$ | $n\text{-}C_pH_{2p+1}$ | F | H | where
m includes all integer values from 0 to 12 inclusive and
p includes all integer values from 0 to 12 inclusive.

TABLE 12
Compounds of the formula:

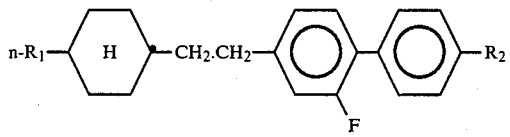

| $R_1$ | $R_2$ |
|---|---|
| $C_mH_{2m+1}$ | $C_pH_{2p+1}$ |
| $C_mH_{2m+1}$ | $OC_pH_{2p+1}$ |
| $C_mH_{2m+1}$ | H |

TABLE 13
Compounds of the formula:

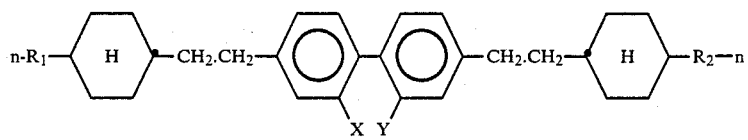

| $R_1$ | $R_2$ | X | Y |
|---|---|---|---|
| $C_mH_{2m+1}$ | $C_pH_{2p+1}$ | F | H |
| $C_mH_{2m+1}$ | $C_pH_{2p+1}$ | H | F | where
m includes all integer values from 0 to 12 inclusive and
p includes all integer values from 0 to 12 inclusive.

EXAMPLE 5

The preparation of 1-(trans-4-n-propylcychohexyl)-2-(2'-fluoro-4'-n-propyl-p-terphenylyl)ethane by Route 5 above.

Step 5a1: The preparation of
3'-Fluoro-4-propyl-p-terphenyl

A solution of 4-(4-n-propylcyclohexenyl)-2-fluorobiphenyl (20 gram) in toluene (120 ml) was added over a 25 minute period with stirring to a suspension of 2,3-dichloro-5,6-dicyano-1,4-benzoquinone (DDQ) (34 gram) in toluene (200 ml). The temperature rose from 19° C. to 24° C. over the addition, after which time the reaction mixture was heated under reflux (114° C.) for 3 hours. The reaction mixture was cooled, filtered, the filtrate and toluene washings (100 ml) were combined and then washed with saturated sodium metabisulphite solution (250 ml). The organic extract was further washed with water (2×250 ml), dried and evaporated to dryness to give a brown residue (20.1 gram). The residue was dissolved in dichloromethane (120 mls) and adsorbed onto a column of basic alumina (60 gram) over silica gel (60 gram). Elution with dichloromethane (450 ml) gave on evaporation of the solvent an off white solid (14 gram) which was recrystallised from ethanol (80 mls) to yield a white crystalline product (12.8 gram) m.p. 75°-77° C.

Step 5b1: The preparation of 4-(trans-4-n-Propylcyclohexylacetyl)-2'-fluoro-4"propyl-p-terphenyl A mixture of 3'-fluoro-4-propyl-p-terphenyl (4 gram) and trans-4-n-propyl-cyclohexylacetyl chloride (2.8 gram) in dichloromethane (15 ml) was added over 20 minutes to a cooled 10° C.) stirred suspension of anhydrous aluminum chloride (2.02 gram) in dichloromethane (10 ml). After the addition the reaction mixture was allowed to warm to 23° C. and left stirring for 18 hours. The resulting solution was added to a 10% hydrochloric acid solution (100 ml) and extracted successively with petroleum spirit (bp 60–80:2×100 ml). The organic extract was then washed with water (120 ml), dried over anhydrous sodium sulphate, filtered and evaporated to dryness. The yellow oily solid (7 gram) was dissolved in dichloromethane (50 ml) and adsorbed onto a column of basic alumina (20 gram) over silica gel (10 gram). Elution with dichloromethane gave on evaporation of the solvent a yellow solid (5 gram). Recrystallisation from dichloroethane (10 gram) gave a crystalline material (2.5 gram) which had the properties: K-S=120–126; S-N=200°–204° C.; N-I=225°–227° C.

Step 5c1: The preparation of 1-(trans-4-n-Propylcyclohexyl)-2-(2'-fluoro-4"-propyl-p-4-terphenyl)ethane The ketone prepared in Step 5b1 (1.8 gram), 99% hydrazine (2 ml) potassium hydroxide (1 gram) and digol (30 ml) were heated with stirring at 120° C. for 17 hours, after which time the temperature was raised by distillation of excess hydrazine hydrate/digol mixture to 180° C. The resulting solution was heated under reflux for 5 hours at 180°-182° C., then cooled to 60° C. and poured into ice water (100 gram). The organic product was extracted with a mixture of petroleum spirit (bp 60-80 150 ml) and dichloromethane (30 ml), washed with water (2×50 ml) and the solvent dried and evaporated. The yellow residue (1.7 gram) was dissolved in 20 ml of a 1:1 mixture of dichloromethane and petroleum spirit (bp 60-80 ) and adsorbed onto a column of basic alumina (6 gram) over silica gel (4 gram). Elution with the same solvent mixture (70 ml) gave on evaporation of solvent a crystalline material (1.3 gram). Recrystallisation from petroleum spirit (bp. 60-80:7 ml) at 10° C. a white solid (1 gram) which had the following properties:

K-S=81-84° C. S-N=86-88° C. N-I=248°-252° C.

Examples of further compounds which may be prepared by one or more of the Routes specified above, or analogous routes, are summarised in Table 13a as follows:

TABLE 13a

Compounds of the formula:

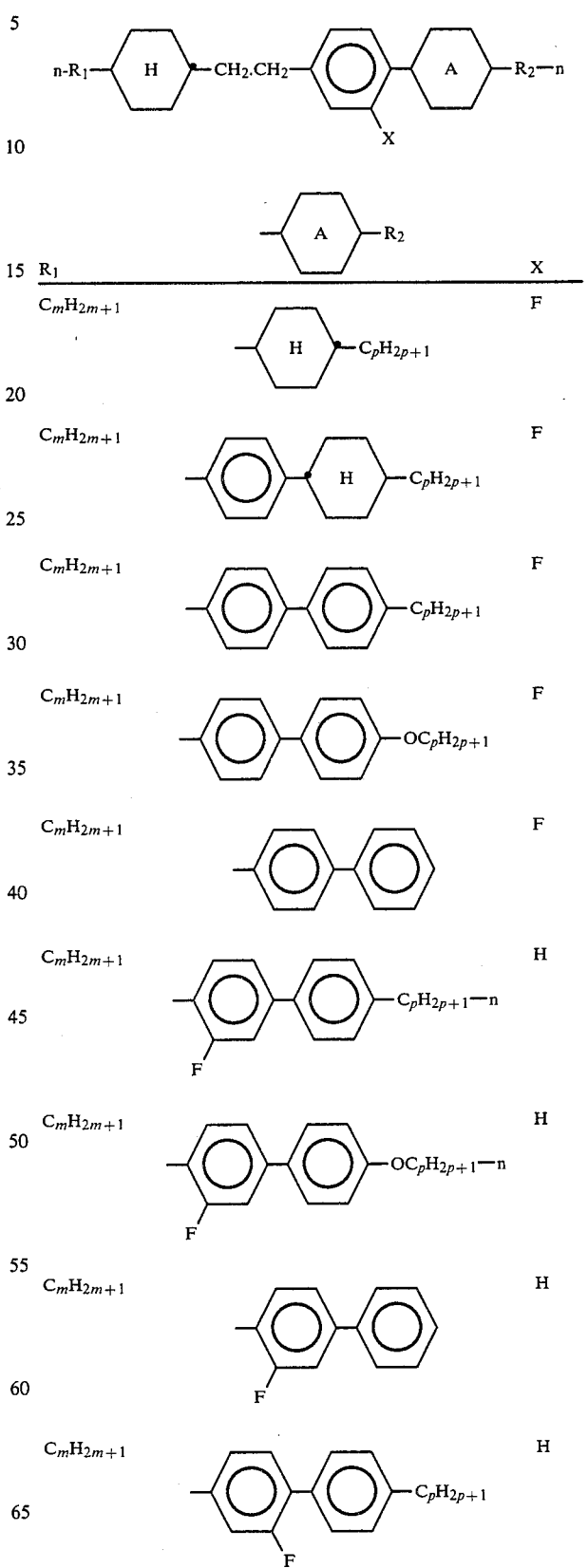

TABLE 13a-continued

Compounds of the formula:

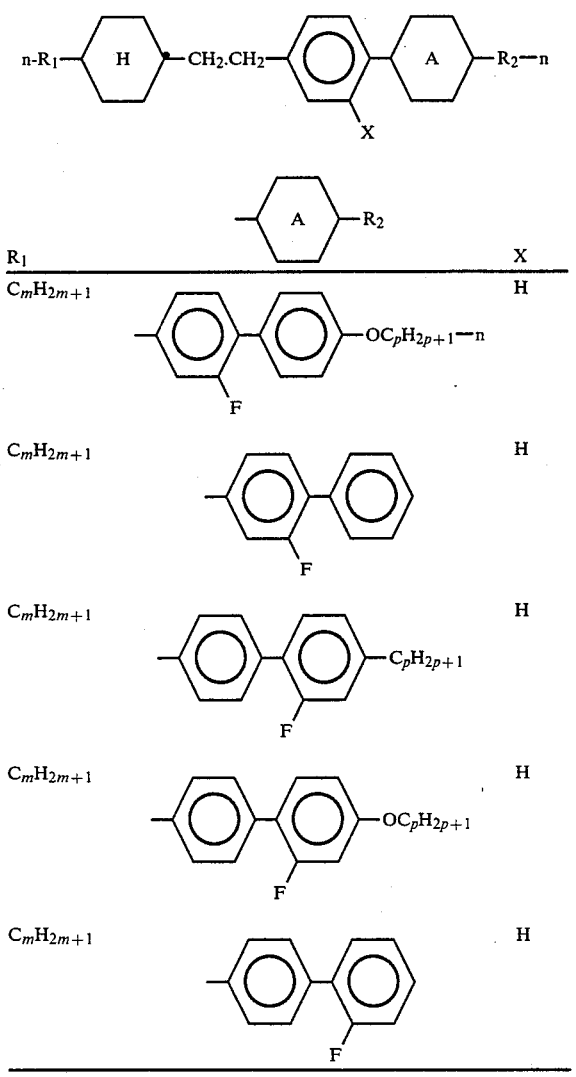

where
m includes all integer values from 0 to 12 inclusive and
p includes all integer values from 1 to 12 inclusive.

The following examples, Example 6 to 8 illustrate the production of compounds of Formula I wherein one of the terminal groups $R_1$ and $R_2$ is chiral.

Example 6:

The preparation of (+)-1-(trans-4-n-butylcyclohexyl)-2-[2'-fluoro-4'(2-methylbutyl)-4-biphenyl]-ethane by Route 1 above:

Step P:

The preliminary preparation of (+)-2 Fluoro-4-(2-methylbutyl)-biphenyl 10 ml of a solution of a 4-bromo-2-fluorobiphenyl (90 gram) in tetrahydrofuran (90 ml) was added to magnesium turnings (9.6 gram) and tetrahydrofuran (20 ml) under nitrogen. A single crystal of iodine was added and the reaction was initiated by warming. The remainder of the solution of 4-bromo-2-fluorobiphenyl was then added dropwise over ½ hour. After heating under reflux for 1 hour, the solution of the Grignard reagent was cooled to 25° C. 10 ml of a solution of 2-methyl-butylphenylsulphonate (150 gram) in tetrahydrofuran (140 ml) was then added to the reaction mixture followed by cuprous chloride (3 gram). The remainder of the phenylsulphonate solution was added over a 40 minute period. The temperature of the resulting grey/-green reaction mixture rose to 45° C. which was then elevated by heating to boiling for 1 hour. The reaction was allowed to cool to room temperature, then added to a 20% (by volume) hydrochloric acid solution (2.5 liters) and the product extracted with dichloromethane (2×500 ml). The organic layer was washed with water (2×500 ml) dried over anhydrous sodium sulphate (15 gram) and the solvent evaporated to give an orange liquid residue. On cooling some white solid crystallised out from the residue. After filtration the residue (88.6 gram) was fractionally distilled under vacuum (0.5 torr) to give a colourless liquid (65 gram). This was found to be 98.8% pure by glc. The bp was 120° C. at 0.5 torr. The optical rotation was +14.62° (solvent).

Step 1a2: The preparation of (+)-4-(trans-4-n-Butylcyclohexylacetyl)-2'-fluoro-4'-(2-methylbutyl)biphenyl A mixture of (+)-2-Fluoro-4(2-methylbutyl)biphenyl (10 gram) and trans-4-n-butylcyclohexylacetyl chloride (9.4 gram) in dichloromethane (20 ml) was added over 20 minutes to a cooled (5°–10° C.), stirred suspension of anhydrous aluminium chloride 6.1 gram) in dichloromethane (20 ml). After the addition the reaction mixture was allowed to warm to 23° C. and left stirring for 17 hours. The resulting solution was added to water (200 ml), extracted successively with petroleum spirit (bp. 60°–80°:180 ml + 100 ml). The organic extract was then washed with water (200 ml), dried over anhydrous sodium sulphate (5 gram) and evaporated. The yellow crystalline residue (17.9 gram) was recrystallised from ethanol (35 ml) at 25° C. to give the product (14.8 gram; 85% yield). The product had mp=71.4°–72.1° C.; VirtualCH-I, (68.5°–68.8° C.). It was found to be 99.5% pure by glc.

Step 1b2: The preparatin of (+)-1-trans-4-n-Butylcyclohexyl)2-[2'-fluoro-4'(2-methylbutyl)-4-biphenylyl]-ethane The ketone prepared above (14.4 gram), 99% hydrazine hydrate (14.4 ml) potassium hydroxide (7.2 gram) and digol (120 ml) were heated and stirring under a reflux condenser at 125° C. for 4 hours, after which time temperature was raised to 175° C. by distillation of the excess hyrazine hydrate. The mixture was then heated under reflux for 17 hours, cooled to 60° C. and poured onto ice water (500 gram). The organic product was extracted with petroleum spirit (bp. 60°–80°:2×200 ml), the extract washed with water (2×200 ml) and dried over anhydrous sodium sulphate. Evaporation of the solvent yielded a yellow oil (14.1 gram). This was dissolved in petroleum spirit (bp. 60–80:100 ml) and absorbed onto a column of basic alumina (50 gram) over silica gel (20 gram). Elution with petroleum spirit (320 ml) gave on evaporation of the solvent a colourless oil (11.7 gram). Crystallisation from propan-1-ol (70 ml) at −50° C. gave a chiral nematic material 9.4 gram; 68% yield). This was found to be 99.8% pure by glc.

The product had the properties:
S-CH,=6° C.; Ch-I 72° C.

Helical molecular pitch=0.23 microns

EXAMPLE 7

The preparation of 1-(trans-4-ethylcyclohexy)-2-[2'-fluoro-4'-(2-methylbutyl)-4-biphenylyl]ethane by Route 1 above

Step 1a3

The preparation of 4-(trans-4-ethylcyclohexylacetyl)-2'-fluoro-4'(2-methylbutyl)biphenyl This was carried out in a manner analogous to Step 1a2 using 4-ethylcyclohexyl acetyl chloride as starting material.

The product had the properties:
Mp=40°–42° C.; virtual Ch-I=(27.5° C.)

Step 1b3

The preparation of 1-(trans-4-ethylcyclohexyl))-2-[2'-fluoro-4'-(2-methylbutyl)-4-biphenylyl]ethane This was carried out in a manner analogous to Step 1b2 above.

This product had the properties:
S-Ch=−11° C. Ch-I=45° C.

EXAMPLE 8

The preparation of 1-(trans-4-n-heptylcyclohexyl)-2-[2'-fluoro-4'-(2-methylbutyl)4-biphenylyl]ethane by Route 1 above

Step 1a4

The preparatin of 4-(trans-4-n-heptylcyclohexylacetyl)-2'-fluoro-4'(2-methylbutyl)biphenyl This was carried out in a manner analogous to Step 1a2 above.

The product had the properties:
K-Ch=69.8°–70.3° C.; Ch-I=74.1°–74.3° C.

Step 1b4

The preparation of 1-(trans-4-n-heptylcyclohexyl)-2-[2'-fluoro-4'-(2-methylbutyl)-4-biphenylyl]ethane This was carried out in a manner analogous to Step 1b2 above.

The product had the properties:
S-Ch=52° C. Ch-I=79° C.

Examples of chiral nematic compounds which may be produced in a manner similar to the above examples are summarised in Table 13b as follows:

TABLE 13b

Compounds of formula:

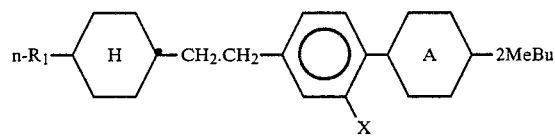

where 2MeBu = (+)-2-methylbutyl

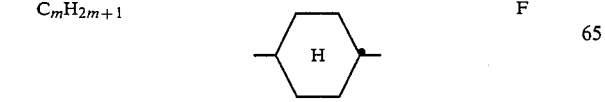

| $R_1$ | A | X |
|---|---|---|
| $C_mH_{2m+1}$ | 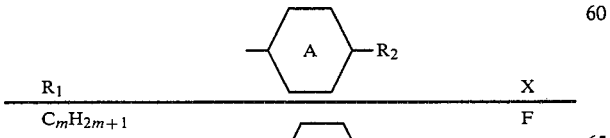 | F |

TABLE 13b-continued

Compounds of formula:

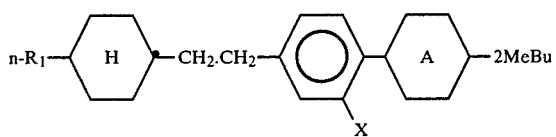

where 2MeBu = (+)-2-methylbutyl

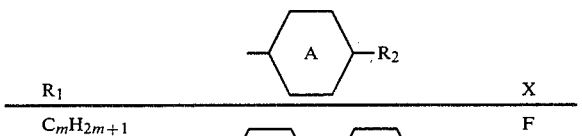

| $R_1$ | A | X |
|---|---|---|
| $C_mH_{2m+1}$ | 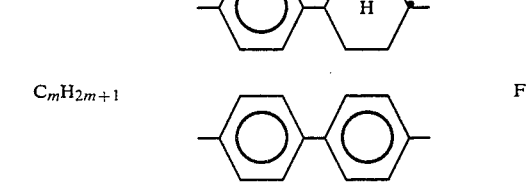 | F |
| $C_mH_{2m+1}$ | 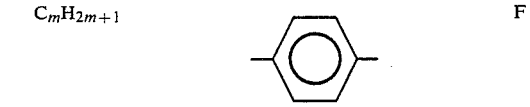 | F |
| $C_mH_{2m+1}$ | (phenyl) | F |
| $C_mH_{2m+1}$ | 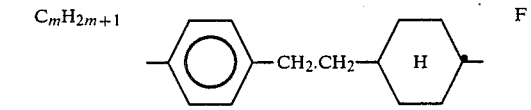 | F |
| $C_mH_{2m+1}$ | 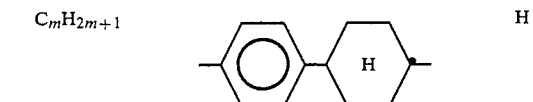 | H |
| $C_mH_{2m+1}$ | 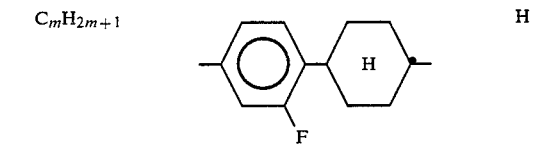 | H |
| $C_mH_{2m+1}$ | 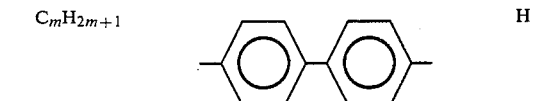 | H |
| $C_mH_{2m+1}$ | 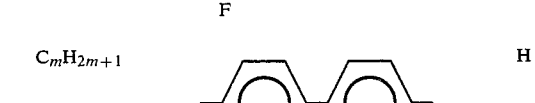 | H |
| $C_mH_{2m+1}$ | 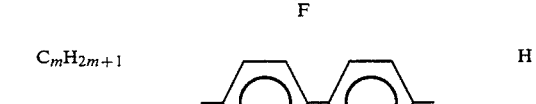 | H |

TABLE 13b-continued

Compounds of formula:

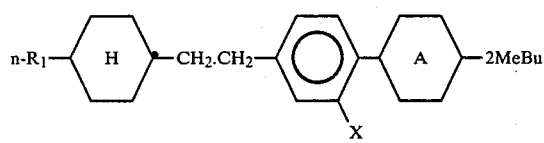

where 2MeBu = (+)-2-methylbutyl

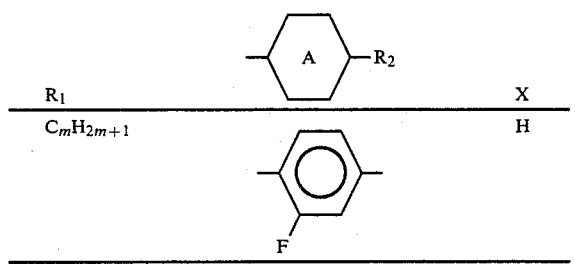

where m includes all values from 0 to 12 inclusive.

The following experiment was carried out to demonstrate the superiority of compounds of Formula Ia having $R_A$=n-alkyl and $R_B$=n-alkyl and less than 10 carbon atoms in $R_A$ and $R_B$ together compared with the compounds of the same formula but with $R_A$ and $R_B$ both n-pentyl, ie a total of 10 carbon atoms in $R_A$ and $R_B$. Each compound under investigation (80% by weight) was separately formed into a mixture together with 10% by weight of the cyanobiphenyl of formula:

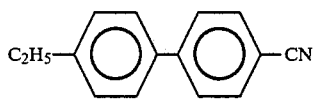

together with 10% by weight of the cyanobiphenylyl ethane of formula:

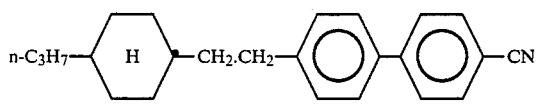

The smectic-to-nematic (S-N) transition temperature of each of the resulting mixtures was then measured. This transition temperature gives a good indication of the tendency of the compound under investigation to form injected smectic phases. The lower the S-N temperature the better is the compound under investigation. The results obtained are listed in Table 14 as follows.

TABLE 14

Investigation of the smectic-to-nematic transition temperatures (S—N) in mixtures for compounds of formula:

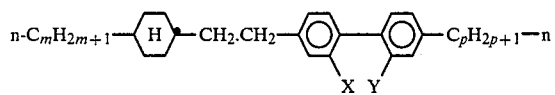

| Compound under investigation | | | | |
|---|---|---|---|---|
| m | p | X | Y | S—N of mixture (°C.) |
| 2 | 2 | H | F | −17.5 |
| 2 | 3 | H | F | −15.2 |
| 2 | 4 | H | F | 14.6 |

TABLE 14-continued

Investigation of the smectic-to-nematic transition temperatures (S—N) in mixtures for compounds of formula:

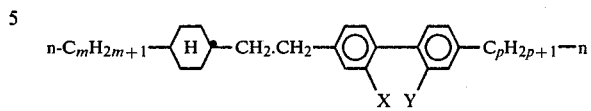

| Compound under investigation | | | | |
|---|---|---|---|---|
| m | p | X | Y | S—N of mixture (°C.) |
| 2 | 5 | H | F | 19.6 |
| 3 | 2 | H | F | −22.0 |
| 3 | 3 | H | F | <−15.0 |
| 3 | 4 | H | F | 29.8 |
| 3 | 5 | H | F | 31.0 |
| 4 | 1 | H | F | <−30.0 |
| 4 | 2 | H | F | 16.0 |
| 4 | 3 | H | F | 28.6 |
| 4 | 4 | H | F | 53.0 |
| 5 | 0 | H | F | <−10 |
| 5 | 2 | H | F | 6.4 |
| 5 | 5* | H | F | 67.5 |
| 2 | 3 | F | H | 1.7 |
| 3 | 2 | F | H | −7.0 |
| 3 | 3 | F | H | 18.5 |
| 5 | 5** | F | H | 76.0 |

The compounds marked * and ** in Table 14 are comparative examples not falling within the scope of the present invention and are clearly inferior, in terms of the S-N value, to the other compounds listed in Table 14.

Similar results are obtained for compounds of Formulae Ia and Ib having $R_1$=n-alkyl and $R_2$=n-alkoxy when the total number of carbon plus oxygen atoms in the groups $R_1$ and $R_2$ is 10 or more.

Examples of materials and devices embodying the invention will now be described by way of example only with reference to the accompanying drawings wherein.

Figure 1:
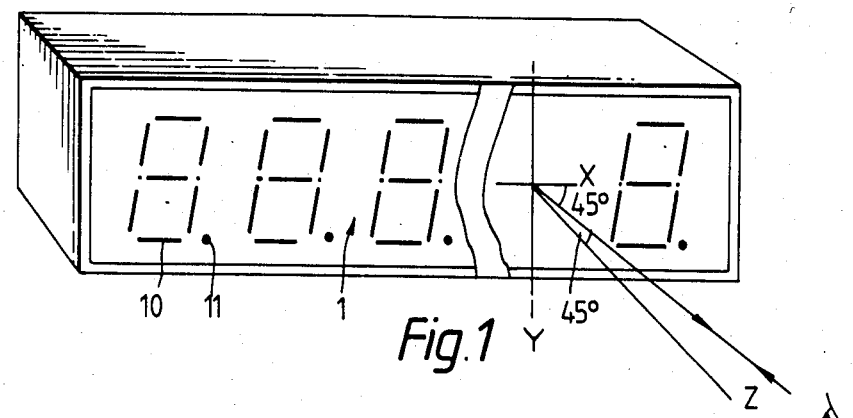
FIG. 1 is a sectional view of a twisted nematic digital display.
Figure 2:
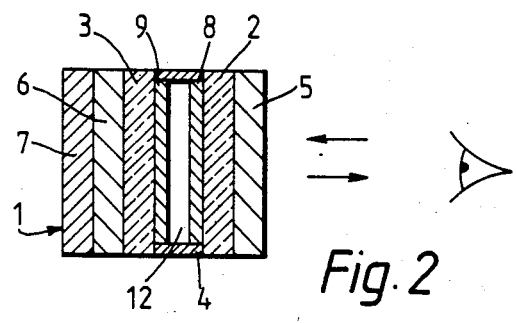
FIG. 2 is a sectional view of the display shown in FIG. 1.

The display of FIGS. 1 to 4 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Figure 3:
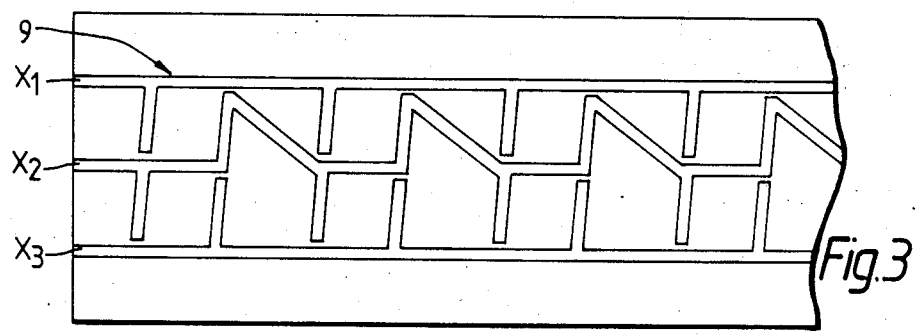
FIG. 3 shows a rear electrode configuration for FIG. 1.
Figure 4:
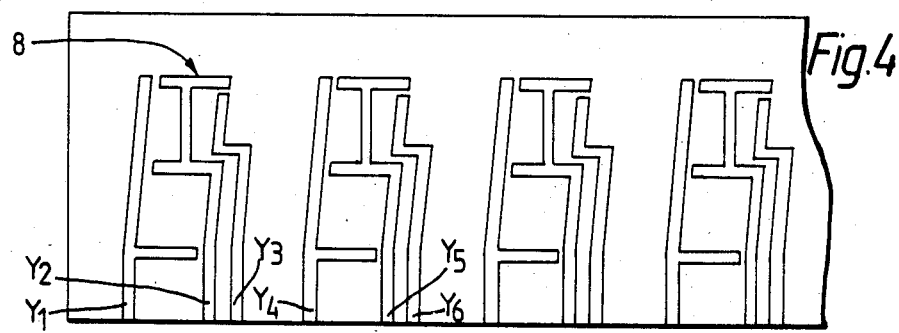
FIG. 4 shows a front electrode configuration for FIG. 1.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes $x_1$, $x_2$, $x_3$. Similarly the front electrode structure is formed into three electrodes per digit and decimal point $y_1$, $y_2$, $y_3$. . . Examination of the six electrodes per digit shows that each of the eight elements can independently have a voltage applied thereto by application of suitable voltage to appropriate x, y electrodes.

Prior to assembly the slides 2, 3 bearing the electrodes are cleaned then dipped in a solution of 0.2% by weight of poly-vinyl alcohol (PVA) in water. When dry, the slides are rubbed in a single direction with a soft tissue then assembled with the rubbing directions orthogonal to one another and parallel to the optical axis of the respective adjacent polarisers, ie so that the polarisers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polariser 5, through the cell 1 (whilst having its plane of polarisation rotated 90°) through its rear polariser 6 to the reflector 7 where it is reflected back again to an observer (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2, 3, ie along the axis Z. Thus light at the position does not reach the reflector 7 and does not reflect back to the observer who sees a dark display of one or more bars of a digit 10.

Figure 5:
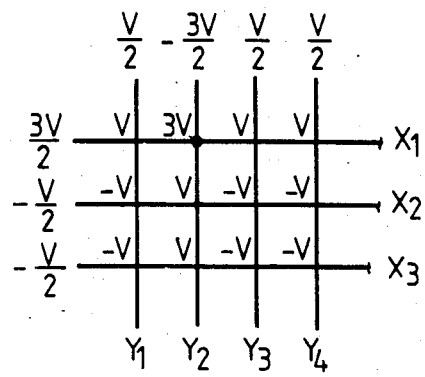
FIGS. 5, 6, 7 show schematic views of the device of FIGS. 1 to 4 with typical addressing voltages.
Figure 6:
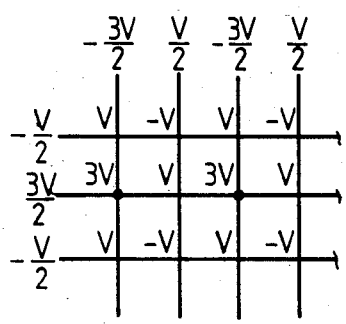
Figure 7:
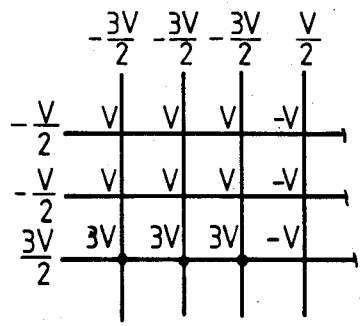

Voltages are applied as follows as shown in FIGS. 5, 6 and 7 for three successive time intervals in a linescan fashion. An electrical potential of 3 V/2 is applied to, ie scanned down, each x electrode in turn whilst $-$V/2 is applied to the remaining x electrodes. Meanwhile $-3$ V/2 or V/2 is applied to the y electrodes. A coincidence of 3 V/2 and $-3$ V/2 at an intersection results in a voltage 3 V across the liquid crystal layer 12. Elsewhere the voltage is V or $-$V. Thus by applying $-3$ V/2 to appropriate y electrodes as 3 V/2 is scanned down the x electrodes selected intersections are turned ON as indicated by solid circles. The electric voltage V is an ac signal of eg 100 Hz square wave, and the sign indicates the phase.

It will be apparent to those skilled in the art that the device shown in FIGS. 1 to 7 is a multiplexed display because the electrodes are shared between ON and OFF intersections or display elements.

Materials embodying the invention which are suitable for use as the material 12 in the above device are Mixtures C, D1, D2, D3 or D4 specified above or Mixture 1 specified in Table 15 as follows.

TABLE 15

| Mixture 1 | |
|---|---|
| Compound | Weight Percentage |
| C₂H₅—◯—◯—CN | 15 |
| n-C₄H₉—◯—◯—CN | 15 |
| C₂H₅—⬡H—◯—CN | 15 |
| n-C₄H₉—⬡H—◯—CN | 15 |

TABLE 15-continued

| Mixture 1 | |
|---|---|
| Compound | Weight Percentage |
| n-C₃H₇—⬡H—CH₂.CH₂—◯—◯(F)—C₃H₇-n | 20 |
| n-C₅H₁₁—⬡H—CH₂.CH₂—◯—◯(F)—C₂H₅ | 20 |

Small amounts of an optically active material may be added to the nematic material to induce a preferred twist in the molecules in the liquid crystal layer. This and the use of appropriate slide surface treatment removes the problems of display patchiness as taught in UK Patent Ser. Nos. 1,472,247 and 1,478,592.

Suitable optically active materials are:

C15: about 0.1–0.5% by weight and CB15: about 0.01% to 0.05% by weight.

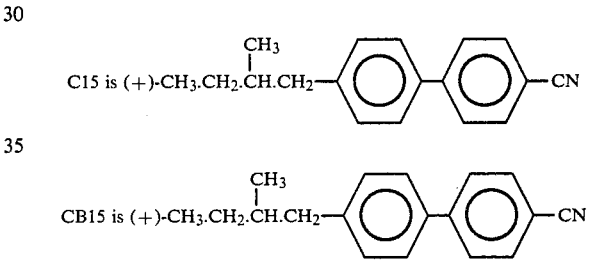

Small amounts of pleochroic dye may be added to enhance the display constrast, eg 2% by weight of dye Mixture 2 specified in UK Patent Specification No. 2093475A. One polariser is removed in this case.

In another embodiment mixtures embodying the second aspect of the invention may be used in a Fréedericksz effect cell. Such a cell may be constructed by sandwiching the liquid crystal material between glass slides having electrode films deposited on their inner surfaces as in the above device. However, in this case the polarisers are not necessary; the glass slide inner surfaces are treated with a coating of lecithin and the liquid crystal material is a negative material whose molecules are aligned in the OFF state perpendicular to the slide substrates (homeotropic texture) by the lecithin coating. Application of an appropriate electric field across the material in the ON state re-arranges the molecules parallel to the slide surfaces (homogeneous texture). A pleochroic dye may be incorporated in the liquid crystal material to enhance the contrast between the ON and OFF states.

A Fréedericksz effect cell made in the above way may incorporate Mixture 3 below, the cell spacing being 10 μm.

TABLE 16

Mixture 3

| Compound | Weight Percentage |
|---|---|
| 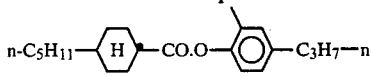 | 30 |
| 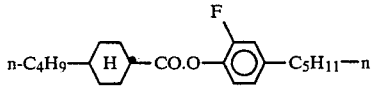 | 30 |
| 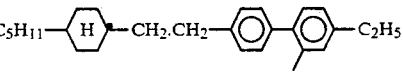 | 20 |
| 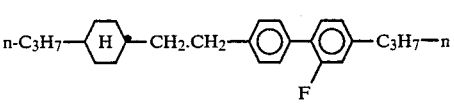 | 20 |

Compound J =

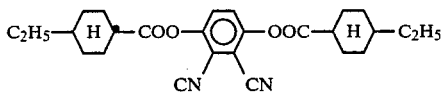

may optionally be added to Mixture 3 (up to 3% by weight of Mixture 3) as a negative additive.

The preparation of Compound J is described in published UK Patent Application No. 2061256A. About 1% by weight of a the dye mixture specified above may be added to Mixture 3 to give a dyed mixture. (Mixture 3A)

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarisers and surface preparations for homogeneous alignment, eg treatment of the glass slide surfaces with SiO, are not used in this case.

If the glass slides are untreated and the liquid crystal material has a positive dielectric anisotropy ($\Delta\epsilon$) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering then the OFF state. This is a 'negative contrast' type of phase change effect device.

If the inner glass slide surfaces are treated, eg with a coating of lecithin, to give alignment perpendicular to those surfaces, and the liquid crystal material has $\Delta\epsilon$ negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (eg 1% by weight of the dye mixture specified above in the case where $\Delta\epsilon$ is positive) to the liquid crystal material.

A suitable positive dielectric anisotropy material, Mixture 4, embodying the invention for use in a phase change effect (negative contrast type) device is:

TABLE 17

Mixture 4

| Compound | Weight Percentage |
|---|---|
| Mixture B { 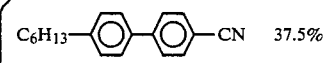 C$_6$H$_{13}$—◯—◯—CN 37.5%<br>n-C$_4$H$_9$—◯—◯—CN 37.5%<br>n-C$_3$H$_7$O—◯—◯—CN 25% } | 50 |
| 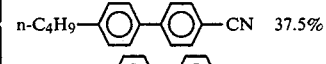 | 23 |
| CB15 = 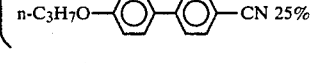<br>($R_c$ = (+)-2-methylbutyl) | 4 |
| 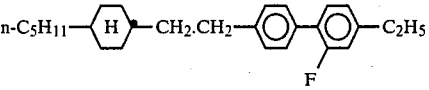 | 23 |

A suitable negative dielectric anisotropy material embodying the invention for use in a phase change effect (positive contrast type) device, Mixture 5, is as follows:

TABLE 18

Mixture 5

| Material | Weight Percentage |
|---|---|
| Mixture 3 | 99 |
| 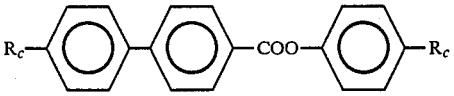<br>($R_c$ = (+)-2-methylbutyl) | 1 |

As an alternative to the chiral compound specified in Table 18 a chiral compound of Formula I may be used.

We claim:

1. A compound having the formula:

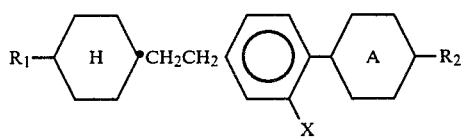

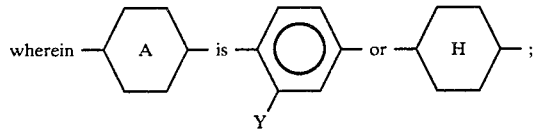

wherein $R_1$ is hydrogen or non-chiral alkyl having up to 12 carbon atoms;

$R_2$ is hyrogen or non-chiral alkyl or non-chiral alkoxy having up to 12 carbon atoms;

each of X and Y independently represent H or F provided that at least one of X and Y is present and is F;

represents a cyclohexane ring which is in the trans configuration if 1,4-disubstituted;

represents a phenylene ring; and the total number of carbon plus oxygen atoms in $R_1$ and $R_2$ is less than 10.

2. A compound as claimed in claim 1, having the formula:

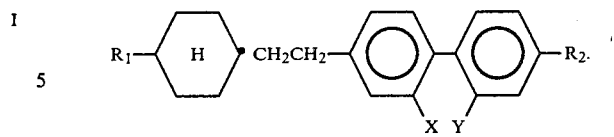

3. A compound as claimed in claim 1, wherein the total number of carbon plus oxygen atoms in $R_1$ and $R_2$ is between 4 and 8 inclusive.

4. A compound as claimed in claim 2, wherein the total number of carbon plus oxygen atoms in $R_1$ and $R_2$ is between 4 and 8 inclusive.

5. A compound as claimed in claim 1, wherein the total number of carbon plus oxygen atoms in $R_1$ and $R_2$ is 5 or less.

6. A compound as claimed in claim 2, wherein the total number of carbon plus oxygen atoms in $R_1$ and $R_2$ is 5 or less.

7. A compound as claimed in claim 1, wherein $R_1$ is n-alkyl and $R_2$ is n-alkyl or n-alkoxy.

8. A compound as claimed in claim 2, wherein $R_1$ is n-alkyl and $R_2$ is n-alkyl or n-alkoxy.

9. A liquid crystal composition comprising a mixture of compounds, at least one being a compound of Formula I, as claimed in claim 1.

10. A liquid crystal composition comprising a mixture of compounds, at least one being a compound as claimed in claim 2.

11. A liquid crystal composition as claimed in claim 9, which contains in addition one or more nematic compounds which contain(s) a terminal cyano group.

12. A liquid crystal composition as claimed in claim 10, which contains in addition one or more nematic compounds which contain(s) a terminal cyano group.

13. In a liquid crystal device including two dielectric substrates at least one of which is optically transparent, a layer of liquid crystal material sandwiched between the said substrates, and electrodes on the inner surfaces of the substrates to enable an electric field to be applied across the layer of liquid crystal material to provide an electro-optic effect therein, the improvement wherein the liquid crystal material includes at least one compound as claimed in claim 1.

* * * * *